(12) United States Patent
Ohrui et al.

(10) Patent No.: US 12,172,942 B2
(45) Date of Patent: Dec. 24, 2024

(54) COMPOSITION, ORGANIC LIGHT-EMITTING DEVICE, DISPLAY DEVICE, PHOTOELECTRIC CONVERSION APPARATUS, ELECTRONIC APPARATUS, AND MOVING OBJECT INCLUDING THE COMPOSITION

(71) Applicant: CANON KABUSHIKI KAISHA, Tokyo (JP)

(72) Inventors: Hiroki Ohrui, Kawasaki (JP); Yosuke Nishide, Kawasaki (JP); Jun Kamatani, Tokyo (JP); Kentaro Ito, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 101 days.

(21) Appl. No.: 18/158,391

(22) Filed: Jan. 23, 2023

(65) Prior Publication Data

US 2023/0159413 A1    May 25, 2023

Related U.S. Application Data

(63) Continuation of application No. 16/660,621, filed on Oct. 22, 2019, now Pat. No. 11,591,279.

(30) Foreign Application Priority Data

Oct. 26, 2018 (JP) ................. 2018-201986
Oct. 3, 2019 (JP) ................. 2019-183349

(51) Int. Cl.
*C07C 15/28* (2006.01)
*H10K 85/60* (2023.01)
(Continued)

(52) U.S. Cl.
CPC ........... *C07C 15/28* (2013.01); *H10K 85/615* (2023.02); *C07C 2603/24* (2017.05);
(Continued)

(58) Field of Classification Search
CPC ...... C07C 15/28; C07C 2603/24; C07B 63/00
See application file for complete search history.

(56) References Cited

U.S. PATENT DOCUMENTS 11,591,279 B2 * 2/2023 Ohrui .................. H10K 85/615

FOREIGN PATENT DOCUMENTS

CN   101087759 A   12/2007
CN   101253150 A   8/2008
(Continued)

OTHER PUBLICATIONS

Jones, et al. "Synthesis of substituted 3-furan-2(5H)-ones via an anthracene Diels-Alder sequence", Tetrahedron Letters, 2006, pp. 4377-4380, vol. 47.

*Primary Examiner* — Vu A Nguyen
(74) *Attorney, Agent, or Firm* — Canon U.S.A., Inc. I.P. Division

(57) ABSTRACT

A composition contains an organic compound and an anthracene compound different from the organic compound, the anthracene compound having a hydrogen atom at at least one of positions 9 and 10, in which the concentration of the anthracene compound is 100 ppm or less. Additionally, a long-lived organic light-emitting device includes an organic compound layer containing a reduced concentration of the anthracene compound.

15 Claims, 6 Drawing Sheets

(51) Int. Cl.
*H10K 50/15* (2023.01)
*H10K 50/16* (2023.01)
*H10K 50/17* (2023.01)
*H10K 50/18* (2023.01)

(52) U.S. Cl.
CPC ............ *H10K 50/15* (2023.02); *H10K 50/16* (2023.02); *H10K 50/171* (2023.02); *H10K 50/18* (2023.02)

(56) References Cited

FOREIGN PATENT DOCUMENTS

| | | | |
|---|---|---|---|
| CN | 102652462 | A | 8/2012 |
| JP | 2004043408 | A | 2/2004 |
| JP | 2015034331 | A | 2/2015 |
| WO | 2010/135395 | A2 | 11/2010 |
| WO | 2018099419 | A1 | 6/2018 |

* cited by examiner

COMPOSITION, ORGANIC LIGHT-EMITTING DEVICE, DISPLAY DEVICE, PHOTOELECTRIC CONVERSION APPARATUS, ELECTRONIC APPARATUS, AND MOVING OBJECT INCLUDING THE COMPOSITION

CROSS-REFERENCE TO RELATED APPLICATIONS

This application is a continuation of U.S. application Ser. No. 16/660,621, filed Oct. 22, 2019, which claims the benefit of Japanese Patent Application Nos. 2018-201986, filed Oct. 26, 2018, and 2019-183349, filed Oct. 3, 2019, each of which is hereby incorporated by reference herein in their entirety.

BACKGROUND OF THE INVENTION

Field of the Invention

The present disclosure relates to a composition in which the concentration of a specific compound in an organic compound layer is reduced, an organic light-emitting device including the composition and thus having a long driving lifetime, a display device, a photoelectric conversion apparatus, a lighting device, an electronic apparatus, and a moving object including the organic light-emitting device.

Description of the Related Art

An organic light-emitting device is an element which includes a pair of electrodes and an organic compound layer disposed between the pair of electrodes. The organic compound is excited by energy obtained by the recombination of a hole and an electron supplied from the electrodes. Light is emitted when the excited energy state returns to the ground state.

Organic light-emitting devices are applied to various devices and required to have improved characteristics. In particular, improvements in driving lifetimes of organic light-emitting devices enable various disadvantages of organic light-emitting devices and devices including them to be solved. Organic light-emitting devices include organic compound layers composed of organic compounds. Organic compounds used in organic compound layers are industrially extracted from, for example, tar, crude oil, or coal as a raw material by various refining methods. In particular, polycyclic aromatic hydrocarbon compounds are often obtained from coal used as a raw material by refining. As a polycyclic aromatic hydrocarbon, anthracene is known.

Japanese Patent Laid-Open No. 2003-282268 (hereinafter, referred to as "PTL 1") describes compound 1-A having an anthracene skeleton and a thiophene skeleton as a light-emitting material. U.S. Patent Application Publication No. 2009/0160326 (hereinafter, referred to as "PTL 2") describes compound 1-B having an anthracene skeleton as an exemplified compound for a blue-light-emitting material having good color purity.

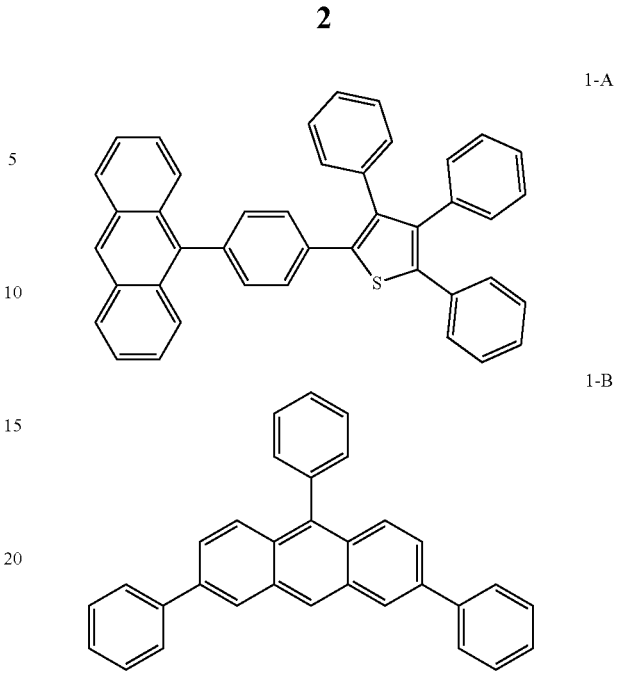

Organic compounds derived from coal contain highly active substances, in some cases. Highly active compounds affect the driving lifetimes of organic light-emitting devices to decrease the driving lifetime. Hitherto, however, it has not been recognized that such a highly active compound is contained. No attempt has been made to improve the driving lifetime of a device by reducing the highly active compound.

PTL 1 and 2 describe highly active compounds such as anthracene compounds, but do not describe the improvement in the lifetimes of devices by reducing the highly active compounds.

SUMMARY OF THE INVENTION

The present disclosure has been made in light of the foregoing disadvantages. The present disclosure provides a composition having a reduced concentration of a highly active compound.

One aspect of the present disclosure is directed to providing a composition containing an organic compound and an anthracene compound different from the organic compound, the anthracene compound having a hydrogen atom at at least one of positions 9 and 10, the concentration of the anthracene compound being 100 ppm or less.

Further features of the present disclosure will become apparent from the following description of exemplary embodiments with reference to the attached drawings.

DESCRIPTION OF THE EMBODIMENTS

Figure 1:
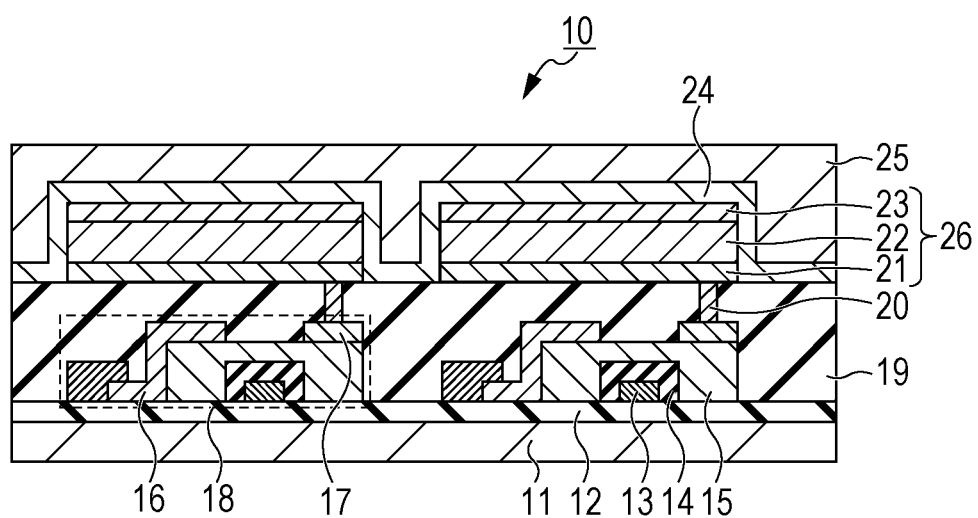
FIG. 1 is a schematic cross-sectional view illustrating an example of a display device including organic light-emitting devices according to an embodiment of the present disclosure and transistors electrically coupled to the organic light-emitting devices.

The present disclosure will be described in detail below.

[1] Anthracene Compound Contained in Composition According to Embodiment of Present Disclosure A composition according to an embodiment of the present disclosure contains an organic compound and an anthracene compound different from the organic compound, the anthracene compound having a hydrogen atom at at least one of positions 9 and 10. When the term "anthracene compound" is simply described in this specification, it refers to an anthracene compound having a hydrogen atom at at least one of positions 9 and 10.

In the composition according to an embodiment of the present disclosure, the concentration of the anthracene compound is preferably 100 ppm or less, more preferably 50 ppm or less, even more preferably 10 ppm or less.

The anthracene compound may be distinguished by a substituent in the anthracene compound. Specific examples thereof include anthracene compounds to which chalcogen atoms are bonded, anthracene compounds consisting only of hydrocarbons, and anthracene compounds having hydroxy groups. When a chalcogen atom or hydroxy group is bonded to the anthracene skeleton, the chalcogen atom or hydroxy group may be directly bonded to the anthracene skeleton or may be bonded to the another substituent bonded to the anthracene skeleton. The concentration of the anthracene compound in which the chalcogen atom is directly bonded to the anthracene skeleton can be reduced.

In the case where multiple types of the anthracene compounds are contained, each of the multiple types of the anthracene compounds may be contained in an amount of 100 ppm or less or 50 ppm or less, preferably 20 ppm or less, more preferably 10 ppm or less. In the case where the multiple types of the anthracene compounds are contained, the total concentration of the multiple types of the anthracene compounds may be 100 ppm or less or 75 ppm or less, preferably 30 ppm or less, more preferably 25 ppm or less.

In the case where more than three types of the anthracene compounds are contained, the concentration of each of any two types of the anthracene compounds can be 20 ppm or less, and the two types of the anthracene compounds can include an anthracene compound in which a chalcogen atom is bonded to its anthracene skeleton.

The concentration of the anthracene compound can be lower and can be equal to or lower than the detection limit thereof. When the anthracene compound is contained in an amount of the detection limit, a small amount of the anthracene compound may be contained. Specifically, the anthracene compound may be contained in an amount of 1 ppm or more, 0.5 ppm or more, or 0.1 ppm or more.

The anthracene compound has a hydrogen atom at at least one of positions 9 and 10. The anthracene compound is highly active at positions 9 and 10. The fact that the anthracene compound has a hydrogen atom at each of the positions, i.e., the anthracene compound is unsubstituted at the positions, indicates that the anthracene compound reacts easily with another compound. When the anthracene compound reacts with another compound, the another compound loses its function. Thus, for example, the driving lifetime of an organic light-emitting device can be shortened.

By reducing the amount of the highly active anthracene compound in the composition to enable organic compounds in the composition to be stably present, the stability of the composition is improved. The stable composition can be present for a long time without losing its function. The use of the stable composition for an organic light-emitting device enables the driving lifetime thereof to be improved.

The composition according to an embodiment of the present disclosure contains an organic compound and an anthracene compound represented by formula [1]. The anthracene compound represented by formula [1] is a compound considered to be contained in the composition together with the organic compound extracted from coal and so forth. However, the present disclosure is not limited to those extracted from coal and so forth as long as the concentration of the anthracene compound in the composition is reduced.

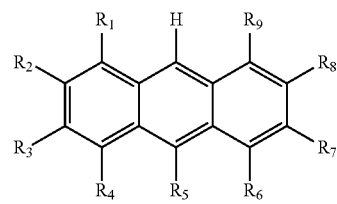

[1]

In formula [1], $R_1$ to $R_9$ are each independently selected from a hydrogen atom, a chalcogen atom, a substituted or unsubstituted alkyl group, a substituted or unsubstituted aryl group, and a substituted or unsubstituted heterocyclic group. $R_1$ to $R_9$ may be the same or different. At least one of $R_1$ to $R_9$ is a substituted or unsubstituted aryl group. Adjacent substituents may form a ring. When at least one of $R_1$ to $R_9$ is a chalcogen atom, adjacent substituents may be bonded to the same chalcogen atom to form a ring. In other words, adjacent substituents among $R_1$ to $R_9$ may form a ring via a chalcogen atom.

Examples of the chalcogen atom in formula [1] include atoms of oxygen, sulfur, and selenium.

In formula [1], the alkyl group may be an alkyl group having 1 to 10 carbon atoms. Specific examples thereof include a methyl group, an ethyl group, a n-propyl group, a n-butyl group, a n-pentyl group, a n-hexyl group, a n-heptyl group, a n-octyl group, a n-decyl group, an isopropyl group, an isobutyl group, a sec-butyl group, a tert-butyl group, an isopentyl group, a neopentyl group, a tert-octyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group. The alkyl group may contain a substituent and may contain a halogen atom. When a halogen atom is contained, the halogen atom can be a fluorine atom. Specific examples thereof include a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, and a 6-fluorohexyl group.

In formula [1], the aryl group may be an aryl group having 6 to 24 carbon atoms. Non-limiting specific examples thereof include a phenyl group, a naphthyl group, an indenyl group, a biphenyl group, a terphenyl group, a fluorenyl group, an anthryl group, a phenanthryl group, a pyrenyl group, a tetracenyl group, a pentacenyl group, a triphenyl group, and a perylenyl group.

In formula [1], the heterocyclic group may be a heterocyclic group having 3 to 21 carbon atoms. Examples of a heteroatom include atoms of oxygen, nitrogen, and sulfur. Non-limiting specific examples thereof include a thienyl group, a pyrrolyl group, a pyridyl group, a pyrazyl group, a pyrimidyl group, a pyridazinyl group, a quinolinyl group, a isoquinolinyl group, an oxazolyl group, an oxadiazolyl group, a phenanthridinyl group, an acridinyl group, a naphthyridinyl group, a quinoxalinyl group, a quinazolinyl group, a cinnolinyl group, a phthalazinyl group, a phenanthrolinyl group, a phenazinyl group, a dibenzofuranyl group, a dibenzothiophenyl group, a carbazolyl group, a benzofuranyl group, a benzothiophenyl group, an indolyl group, a cycloazyl group, a benzimidazolyl group, a benzothiazolyl group, and a benzothiadiazolyl group.

In formula [1], examples of a substituent attached to the substituents, i.e., the alkyl group, the aryl group, and the heterocyclic group, include alkyl groups having 1 to 6 carbon atoms such as a methyl group, an ethyl group, a propyl group, and a butyl group; aralkyl groups such as a benzyl group; aryl groups having 6 to 12 carbon atoms such as a phenyl group and a biphenyl group; heterocyclic groups having 3 to 9 carbon atoms such as a pyridyl group, a pyrrolyl group, a benzimidazolyl group, and a benzothiazolyl group; amino groups such as a dimethylamino group, a diethylamino group, a dibenzylamino group, a diphenylamino group, and a ditolylamino group; alkoxy groups such as a methoxy group, an ethoxy group, a propoxy group, and a phenoxy group; a cyano group; and halogen atoms such as fluorine atoms. Examples of heteroatoms in the heterocyclic group include atoms of oxygen, nitrogen, and sulfur.

Positions 9 and 10 of the anthracene skeleton are easily subjected to halogenation and oxidation because of their high chemical reaction activity. Thus, various substituents can be easily provided at positions 9 and 10 by subjecting the anthracene skeleton to halogenation and then a coupling reaction with various boronic acids in the presence of a metal catalyst. The substituents provided can be stably present.

However, in an anthracene compound in which hydrogen atoms are present at both of the 9- and 10-positions, the hydrogen atoms located at these positions are easily eliminated to generate radicals. The positions where the hydrogen atoms have been eliminated are easily oxidized or reacted with another compound. In other words, the anthracene compound in which hydrogen atoms are located at both positions 9 and 10 is in an unstable state.

In the case where a hydrogen atom is located at either position 9 or position 10 of an anthracene skeleton, in other words, in the case where a substituent is located at one of the positions, the effect of the electron-donating properties of the substituent further increases the reaction activity at position 9 or 10 where the hydrogen atom is located. Thus, the anthracene compound is unstable as described above.

Thus, in the case where a hydrogen atom is located at at least one of positions 9 and 10 of the anthracene skeleton, the compound is unstable.

The use of the anthracene compound represented by formula [1] does not merely destabilize the composition. In the case where the anthracene compound represented by formula [1] is mixed in the organic layer, particularly in the light-emitting layer, of an organic light-emitting device, the anthracene compound acts as an exciton quencher to cause a decrease in luminance during continuous current driving. Furthermore, the anthracene compound acts as a charge trap for electrons or holes, and breaks the carrier balance in the light-emitting layer during continuous current driving to generate excess electrons or holes. The excessive electrons or holes eventually act as exciton quenchers to cause a decrease in luminance.

The anthracene compound represented by formula [1] is contained in organic compounds refined from coal, crude oil, or tar. As the organic compounds, for example, polycyclic aromatic hydrocarbons such as an anthracene compound represented by formula [2] are known. An impurity contained in a process for synthesizing such a polycyclic aromatic hydrocarbon is the anthracene compound represented by formula [1]. In the case where the relative purity thereof in the organic compound layer of an organic light-emitting device is measured by high-performance liquid chromatography and found to be 0.01% or less, i.e., 100 ppm or less, the driving lifetime of the organic light-emitting device can be significantly improved.

Examples of the polycyclic aromatic hydrocarbon include compounds represented by formulae [2] to [6]. The compounds represented by formulae [2] to [6] are examples of the polycyclic aromatic hydrocarbon, and embodiments of the present disclosure are not limited thereto.

The compounds represented by formulae [2] to [6] are examples of the polycyclic aromatic hydrocarbon. In the course of refining or extraction, the polycyclic aromatic hydrocarbon can contain an anthracene compound having a hydrogen atom at at least one of positions 9 and 10. The polycyclic aromatic hydrocarbon is obtained from a raw material such as tar, crude oil, or coal and thus can contain, as an impurity, an anthracene compound having a hydrogen atom at at least one of positions 9 and 10.

The compound represented by formula [2] is an example of the polycyclic aromatic hydrocarbon and is an anthracene compound having a sub stituent other than a hydrogen atom at each of positions 9 and 10.

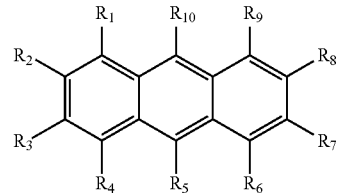

[2]

In formula [2], $R_1$ to $R_{10}$ are substituents each independently selected from a hydrogen atom, a substituted or unsubstituted alkyl group, a substituted or unsubstituted aryl group, and a substituted or unsubstituted heterocyclic group, and may be the same or different, provided that at least one of $R_1$ to $R_9$ is a substituted or unsubstituted aryl group and that neither $R_5$ nor $R_{10}$ is a hydrogen atom.

The anthracene compound represented by formula [1] is contained also in polycyclic aromatic hydrocarbon compounds represented by formulae [3] to [6]. This is because pyrene, chrysene, phenanthrene, and triphenylene, which are basic skeletons of compounds represented by formulae [3] to [6], are polycyclic aromatic hydrocarbons extracted by variously refining a raw material such as tar, crude oil, or coal, similarly to anthracene.

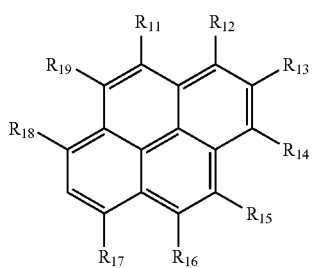

[3]

In formula [3], $R_{11}$ to $R_{19}$ are substituents each independently selected from a hydrogen atom, a substituted or unsubstituted alkyl group, a substituted or unsubstituted aryl group, and a substituted or unsubstituted heterocyclic group, and may be the same or different. At least one of $R_{11}$ to $R_{19}$ may be a substituted or unsubstituted aryl group.

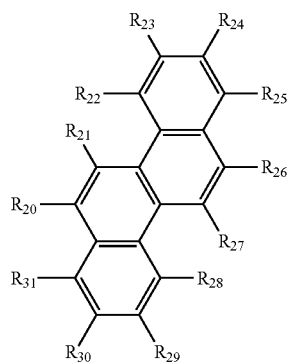

[4]

In formula [4], $R_{20}$ to $R_{31}$ are substituents each independently selected from a hydrogen atom, a substituted or unsubstituted alkyl group, a substituted or unsubstituted aryl group, and a substituted or unsubstituted heterocyclic group, and may be the same or different. At least one of $R_{20}$ to $R_{31}$ may be a substituted or unsubstituted aryl group.

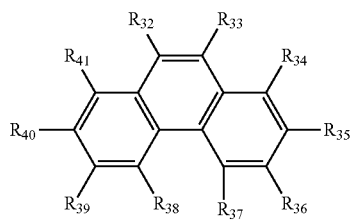

[5]

In formula [5], $R_{32}$ to $R_{41}$ are substituents each independently selected from a hydrogen atom, a substituted or unsubstituted alkyl group, a substituted or unsubstituted aryl group, and a substituted or unsubstituted heterocyclic group, and may be the same or different. At least one of $R_{32}$ to $R_{41}$ may be a substituted or unsubstituted aryl group.

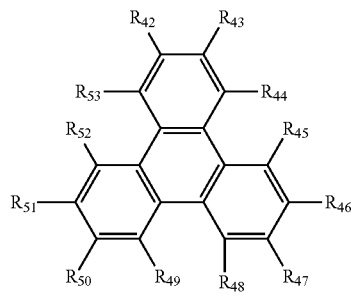

[6]

In formula [6], $R_{42}$ to $R_{53}$ are substituents each independently selected from a hydrogen atom, a substituted or unsubstituted alkyl group, a substituted or unsubstituted aryl group, and a substituted or unsubstituted heterocyclic group, and may be the same or different. At least one of $R_{42}$ to $R_{53}$ may be a substituted or unsubstituted aryl group.

A composition according to an embodiment of the present disclosure can contain a polycyclic aromatic hydrocarbon represented by one of formulae [2] to [6] and the anthracene compound represented by formula [1], in which the composition can contain 100 ppm or less of the anthracene compound represented by formula [1]. At an anthracene compound content of 100 ppm or less, the stability of the composition can be improved to significantly improve the driving lifetime of an organic light-emitting device including the composition.

The anthracene compound represented by formula [1] often contains a chalcogen atom bonded thereto. This is because tar, crude oil, or coal, which is used as a raw material when a polycyclic aromatic hydrocarbon is industrially refined, contains chalcogen atoms. Such a chalcogen atom in the raw material is not removed in an extraction step or refinement step and is bonded to a final product, in some cases. The chalcogen atom may be a sulfur atom.

In an anthracene compound which is represented by formula [1] and to which a chalcogen atom is bonded, the reaction activity at positions 9 and 10 is further increased by the electron-donating properties of the chalcogen atom. In the case where at least one of positions 9 and 10 is a hydrogen atom, the anthracene compound has high reactivity and thus is unstable, as described above. In particular, in the case where a sulfur atom is bonded as a chalcogen atom, high reactivity is exhibited. Accordingly, in the case where the anthracene compound represented by formula [1] contains a sulfur atom, the anthracene compound is highly effective in reducing the anthracene concentration to 100 ppm or less.

[2] Method for Reducing Anthracene Compound Represented by Formula [1]

The anthracene compound represented by formula [1] is referred to as an "impurity", in some cases. This is because the anthracene compound is unintentionally formed during refining to degrade the performance of a target object. In the past, for example, halogen atoms have been recognized as impurities, and the impurities have been reduced by, for example, sublimation purification.

The sublimation purification is a method for separating compounds using different sublimation temperatures of compounds. Sublimation temperature is affected by the molecular weight of a compound. Thus, compounds having similar molecular weights tend to have close sublimation temperatures. It is difficult to separate an anthracene compound having a hydrogen atom at at least one of positions 9 and 10 from an organic compound having a sublimation temperature close to the anthracene compound, in some cases. In particular, in the case where the organic compound is a polycyclic aromatic hydrocarbon, it is difficult to separate the anthracene compound by sublimation purification because these compounds have close sublimation temperatures. In particular, in the case where the impurity and a target organic compound are different in the bonding of a chalcogen atom, it is difficult to separate them because of a small difference in molecular weight therebetween.

To reduce the concentration of the anthracene compound represented by formula [1], the anthracene compound can be separated at a stage where the molecular weight is low. In the case of a low molecular weight, the proportion of the impurity is high even at a small difference in molecular weight, thus increasing the proportion of the impurity. For example, industrial purification can be performed at the stage of a low-molecular-weight raw material such as unsubstituted pyrene or a halogenated pyrene.

It is possible to employ a method for selectively reducing or removing the anthracene compound represented by formula [1] by subjecting the anthracene compound represented by formula [1] to a chemical reaction.

An example of the method is the Diels-Alder reaction using the anthracene compound represented by formula [1] as a conjugated diene. In this case, the anthracene compound represented by formula [1] can have a hydrogen atom at each of positions 9 and 10. For example, maleic anhydride can be used as a dienophile. In the case where the anthracene compound has a hydrogen atom at each of positions 9 and 10, when maleic anhydride is used as a dienophile, maleic anhydride is selectively added to positions 9 and 10 of the anthracene compound. An adduct formed by the reaction differs in polarity from the anthracene represented by formula [1]. Thus, the anthracene compound can be separated from a target organic compound having a polycyclic aromatic hydrocarbon as a basic skeleton by adsorption treatment such as column purification.

Another example of the method is reaction with peroxide. The reaction of the anthracene compound represented by formula [1] with a peroxide changes the polarity of the anthracene compound. Thus, the anthracene compound can be separated by, for example, the column purification. Specifically, the case where a sulfur atom is bonded as a chalcogen atom to the anthracene skeleton will be described below. The sulfur atom bonded to the anthracene skeleton is selectively oxidized into sulfoxide by reaction with peroxide. In contrast, a polycyclic aromatic hydrocarbon that does not contain a sulfur atom does not react with peroxide, so that the polarity of the polycyclic aromatic hydrocarbon does not change. Owing to a difference in polarity between the anthracene compound represented by formula [1] and a target organic compound, the anthracene compound can be separated by adsorption treatment such as column purification in the same way as above.

The anthracene compound represented by formula [1] can be selectively reacted and separated from a composition containing a compound having a polycyclic aromatic hydrocarbon as a basic skeleton through the use of these reactions to reduce the concentration of the anthracene compound represented by formula [1].

[3] Organic Light-Emitting Device According to Embodiment of Present Disclosure

An organic light-emitting device according to an embodiment may include a first electrode, a second electrode, and an organic compound layer disposed between the first electrode and the second electrode. The first electrode and the second electrode may be an anode and a cathode, which are a pair of electrodes. In the organic light-emitting device according to the embodiment, the organic compound layer may be formed of a single layer or a stack of multiple layers as long as a light-emitting layer is included.

In the case where the organic compound layer is formed of the stack of multiple layers, the organic compound layer may include, for example, a hole injection layer, a hole transport layer, an electron-blocking layer, a hole-exciton-blocking layer, an electron transport layer, and an electron injection layer, in addition to the light-emitting layer. The light-emitting layer may be formed of a single layer or a stack of multiple layers. In the case where the organic compound layer is formed of stack of multiple layers, the organic compound layer may include, from the anode side, the hole injection layer, the hole transport layer, the electron-blocking layer, the light-emitting layer, the hole-blocking layer, the electron transport layer, and the electron injection layer.

The LUMO level of the electron-blocking layer can be higher than that of the light-emitting layer. This is because the transfer of electrons from the light-emitting layer toward the anode side is reduced. The HOMO level of the hole-blocking layer can be lower than that of the light-emitting layer. This is because the transfer of holes from the light-emitting layer toward the cathode side is reduced.

Here, the HOMO refers to the highest occupied molecular orbital, and the LUMO refers to the lowest unoccupied molecular orbital. A high HOMO level and a high LUMO level indicate a state closer to the vacuum level. A high HOMO level is also referred to as a shallow HOMO level. The same applies to the LUMO.

The organic compound layer of the organic light-emitting device according to the embodiment preferably contains 10 ppm or less, more preferably 5 ppm or less, even more preferably 1 ppm or less of an anthracene compound having a hydrogen atom at at least one of positions 9 and 10. In Examples of this specification, the measurement limit is less than 5 ppm; however, measurement can be performed by another method.

The organic compound layer including multiple layers stacked may be disposed between the first electrode and the second electrode. Only the organic compound layer may be disposed between the first electrode and the second electrode. The organic compound layer may be in contact with the first electrode and the second electrode. In this case, the organic compound layer may contain 5 ppm or less of the anthracene compound.

The concentration of the anthracene compound in the hole transport layer can be lower than the concentration of the anthracene compound in the light-emitting layer.

The concentration of the anthracene compound in the electron transport layer can be lower than the concentration of the anthracene compound in the light-emitting layer.

In the organic light-emitting device according to the embodiment, at least one layer in the organic compound layer contains a composition according to the embodiment. Specifically, the composition according to the embodiment is contained in any of, for example, the hole injection layer, the hole transport layer, the electron-blocking layer, the light-emitting layer, the hole-exciton-blocking layer, the electron transport layer, and the electron injection layer. The composition according to an embodiment of the present disclosure can be contained in the light-emitting layer.

In the organic light-emitting device according to the embodiment, in the case where the composition according to the embodiment is contained in the light-emitting layer, the light-emitting layer may be a layer consisting only of the composition according to the embodiment or may be a layer composed of the composition according to the embodiment and another compound.

The light-emitting layer may contain a host serving as a first compound and may contain a guest serving as a second compound. The light-emitting layer may include, from the anode side, a first light-emitting layer and a second light-emitting layer. The second light-emitting layer may be in contact with the cathode side of the first light-emitting layer. The first light-emitting layer may include a first host, a first guest, and a second guest. The second light-emitting layer may include a second host and a third guest. The first host and the second host may be an identical compound.

Here, the host refers to a compound having the highest proportion, by weight, of compounds constituting the light-emitting layer. The guest refers to a compound that has a lower proportion, by weight, than the host in the compounds constituting the light-emitting layer and that is responsible for main light emission. The guest is also referred to as a dopant, in some cases. An assist material refers to a compound that has a lower proportion, by weight, than the host in the compounds constituting the light-emitting layer and that assists the light emission of the guest. The assist material is also referred to as a second host.

The inventors have conducted various studies and have found that in the case where a composition according to an embodiment of the present disclosure is used for the organic compound layer of the organic light-emitting device, a device that emits light with high efficiency, high luminance, and very high durability can be obtained. The organic compound layer includes the light-emitting layer. The light-emitting layer may be formed of a single layer or multiple layers. One light-emitting layer may contain light-emitting materials that emit light beams of different emission colors. The light-emitting device can emit white light by a combination of light beams of multiple emission colors. The term "multiple layers" used here refers to a state in which a light-emitting layer and another light-emitting layer are stacked. Stacking refers to a state in which the organic compound layers are stacked in the direction from one electrode to the other electrode.

The composition according to an embodiment of the present disclosure can be used as the constituent material of an organic compound layer other than the light-emitting layer included in the organic light-emitting device according to the embodiment. Specifically, the composition may be used as the constituent material of, for example, the electron transport layer, the electron injection layer, or the hole-blocking layer. The composition can be used as the constituent material of the hole-blocking layer adjacent to the light-emitting layer.

The structure of the organic light-emitting device according to the embodiment is not limited thereto. For example, the following various layer structures may be used: Insulating layers are disposed at interfaces between the electrodes and the organic compound layer. An adhesive layer or an interference layer is disposed. The electron transport layer or the hole transport layer is formed of two layers having different ionization potentials.

The light extraction structure of the organic light-emitting device may be a top emission structure in which light emerges from the electrode opposite to a substrate, may be a bottom emission structure in which light emerges from the substrate, or may be a structure in which light emerges from both sides. In the case where light emerges from the substrate, the substrate and the electrode adjacent to the substrate can be optically transparent. In the case where light emerges from the opposite side to the substrate, the electrode opposite to the substrate can be optically transparent.

In the organic light-emitting device according to the embodiment, a known compound may be used together with the composition according to the embodiment of the present disclosure, as needed. Specific examples of the known compound include low-molecular-weight and high-molecular-weight hole injection compounds and hole transport compounds, compounds serving as a host, light-emitting compounds, electron injection compounds, and electron transport compounds. Examples of these compounds will be illustrated below.

As a hole injection-transport material, a material having a high hole mobility can be used so as to facilitate the injection of holes from the anode and to transport the injected holes to the light-emitting layer. To reduce a degradation in film quality in the organic light-emitting device, such as crystallization, a material having a high glass transition temperature can be used.

Examples of low-molecular-weight and high-molecular-weight materials having hole-injecting and hole-transporting properties include triarylamine derivatives, aryl carbazole derivatives, phenylenediamine derivatives, stilbene derivatives, phthalocyanine derivatives, porphyrin derivatives, poly(vinyl carbazole), polythiophene, and other conductive polymers. Furthermore, the hole injection-transport materials are appropriately used also for the electron blocking layer.

Non-limiting specific examples of a compound used as the hole injection-transport material will be illustrated below.

HT1

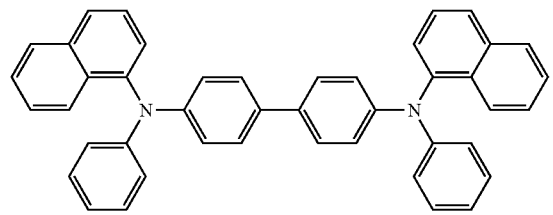

HT2

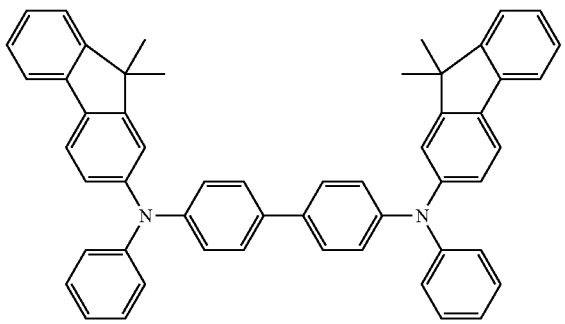

-continued
HT3
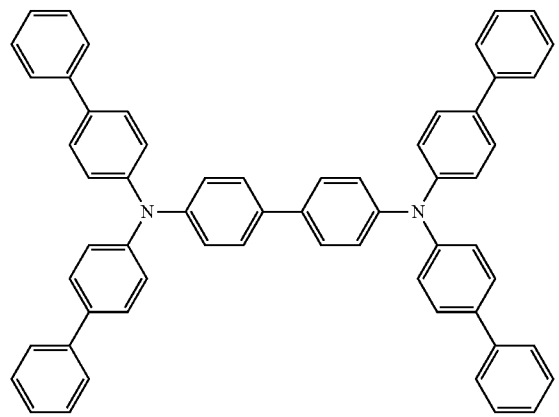
HT4
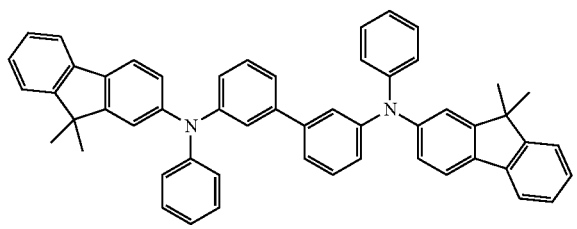
HT5
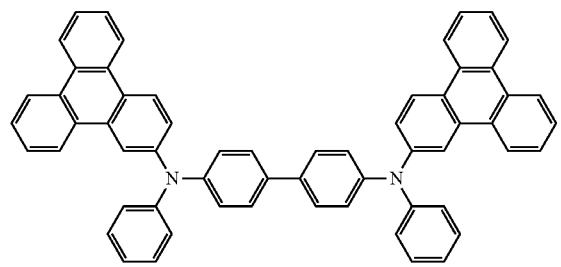
HT6
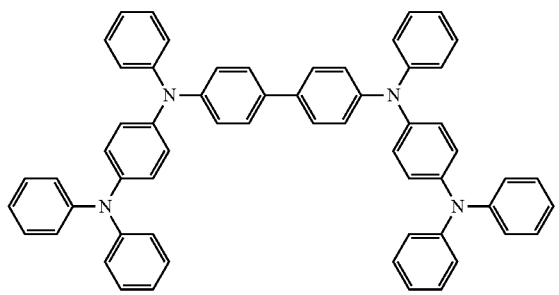
HT7
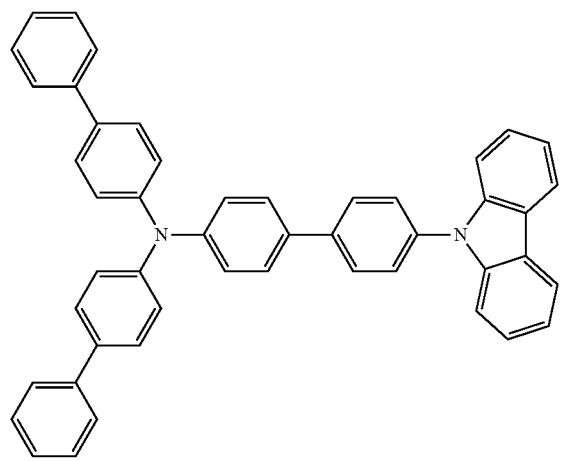
HT8
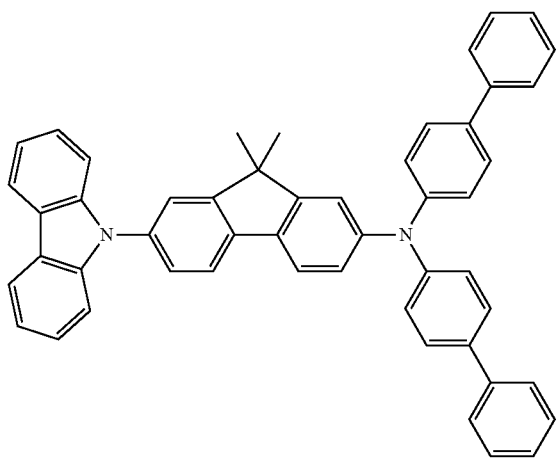

-continued
HT9
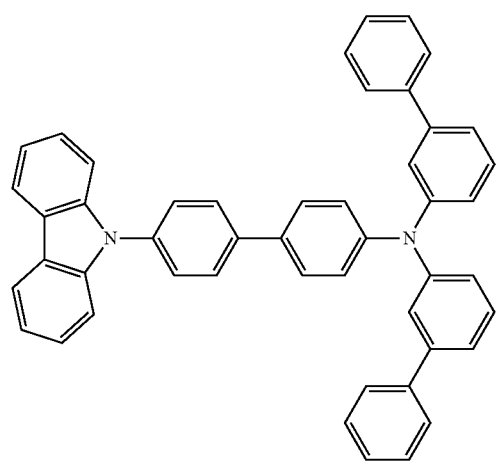
HT10
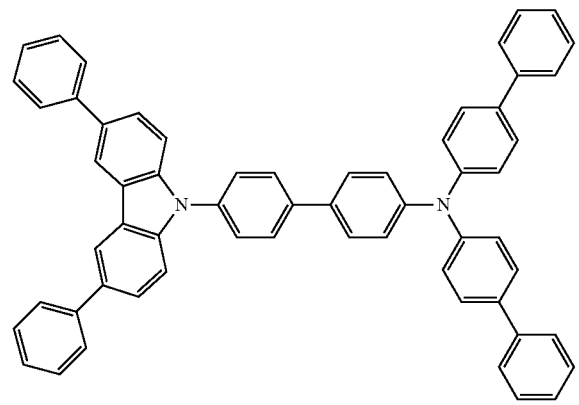
HT11
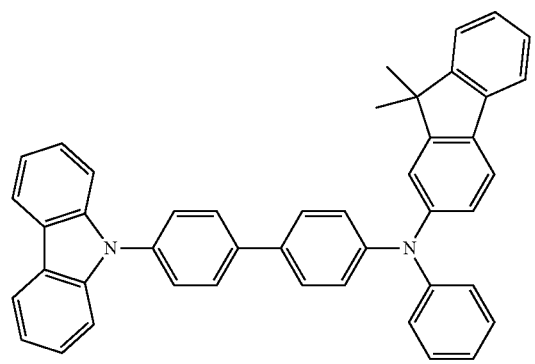
HT12
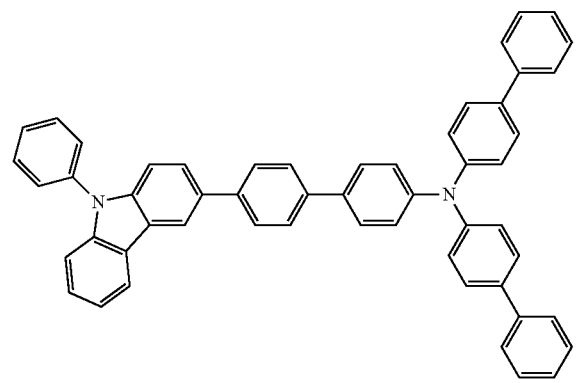
HT13
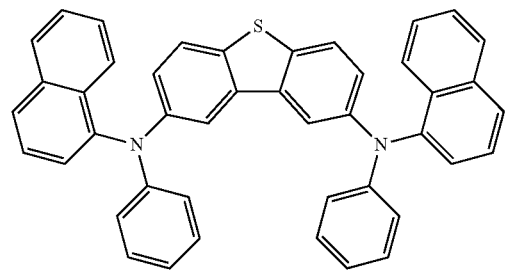
HT14
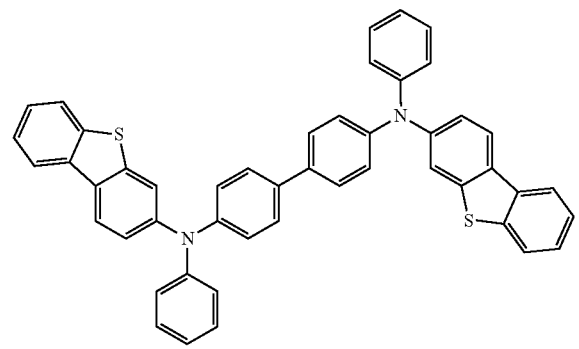

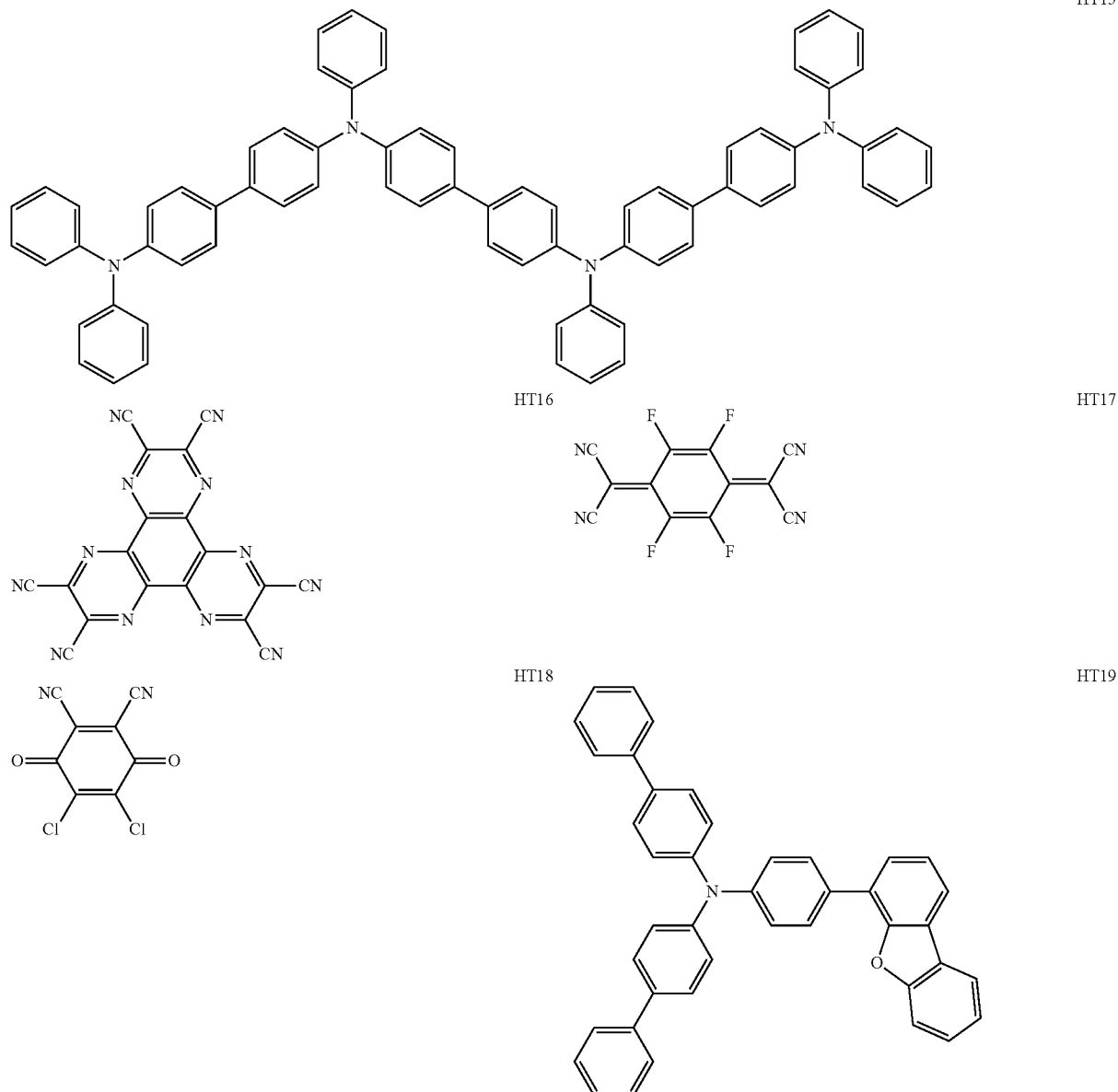

Among the hole transport materials illustrated above, HT16 to HT18 can be used for a layer in contact with the anode to reduce the driving voltage. HT16 is widely used in organic light-emitting devices. HT2, HT3, HT10, and HT12 may be used for an organic compound layer adjacent to a layer composed of HT16. Multiple materials may be used for one organic compound layer. For example, a combination of HT2 and HT4, a combination of HT3 and HT10, or a combination of HT8 and HT9 may be used.

Examples of a light-emitting material mainly associated with a light-emitting function include condensed-ring compounds such as fluorene derivatives, naphthalene derivatives, pyrene derivatives, perylene derivatives, tetracene derivatives, anthracene compounds, and rubrene, quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene)derivatives, polyfluorene derivatives, and polyphenylene derivatives. The term "derivative" indicates a compound whose skeleton can be found in its structure. For example, BD3 below can be referred to as a fluorene derivative. BD6, BD7, GD4, and RD1 can be referred to as fluoranthene derivatives. GD1, GD2, and GD3 can be referred to as anthracene derivatives. GD5 is an anthracene derivative as well as a pyrene derivative. Among these, fluoranthene derivatives, anthracene derivatives, and pyrene derivatives can be used. In the case where multiple light-emitting materials are used, all the light-emitting materials can be fluoranthene derivatives, anthracene derivatives, or pyrene derivatives.

Non-limiting specific examples of a compound used as a light-emitting material will be illustrated below.

BD1
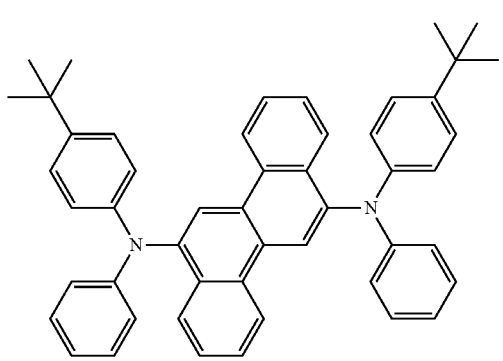
BD5
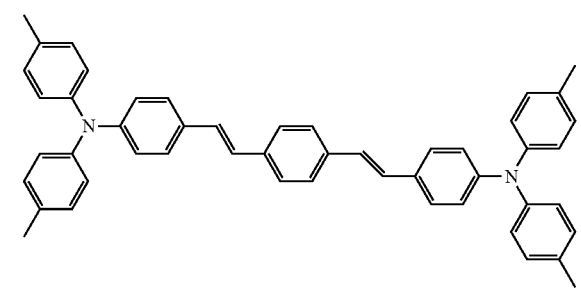
BD2
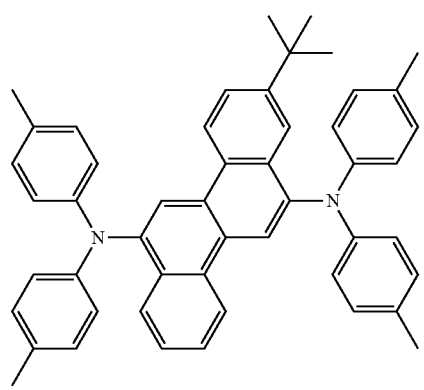
BD6
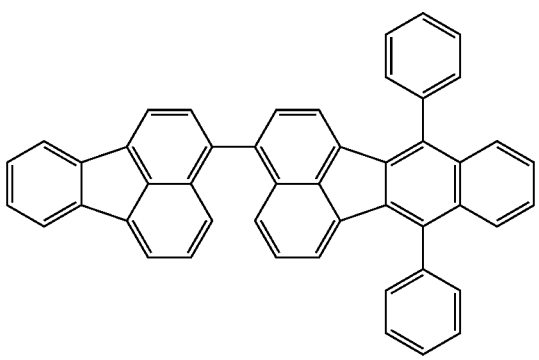
BD3
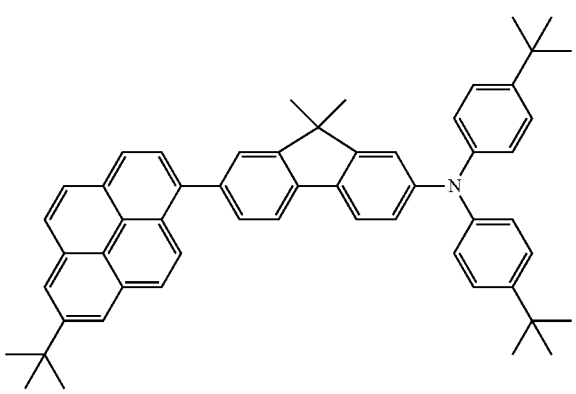
BD7
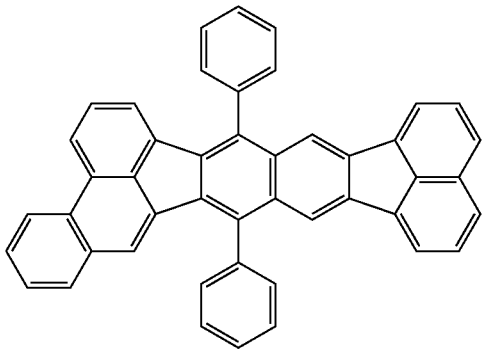
BD4
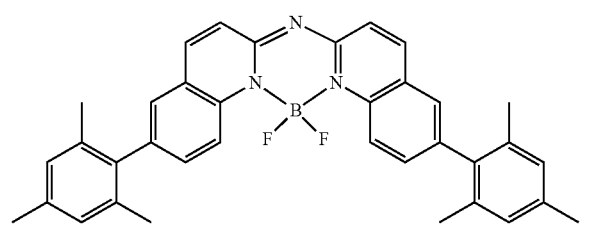
BD8
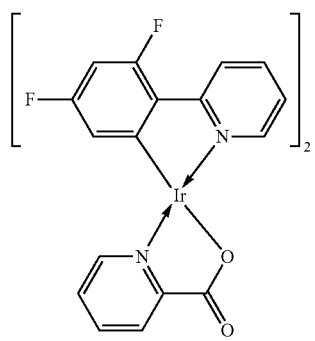

-continued
GD1
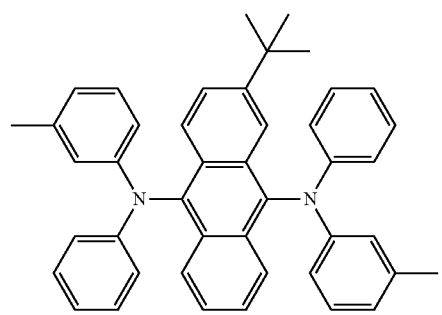
GD2
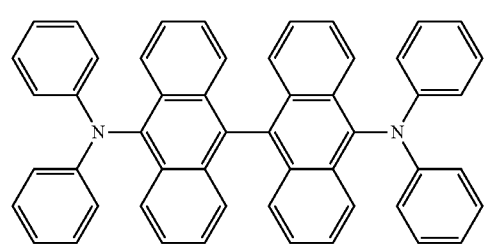
GD3
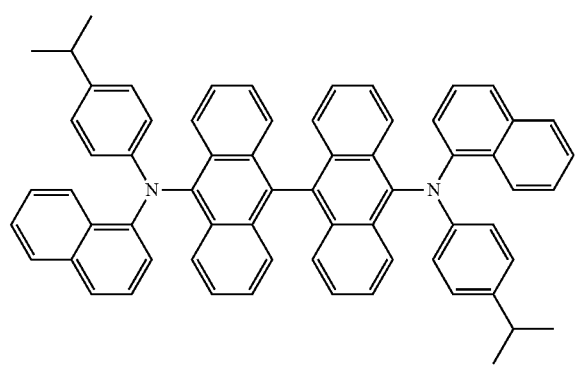
GD4
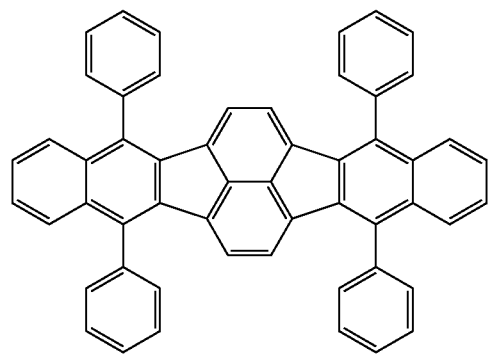
-continued
GD5
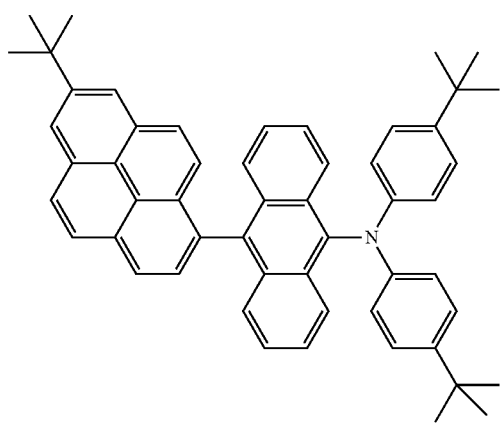
GD6
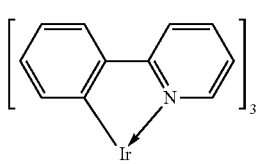
GD7
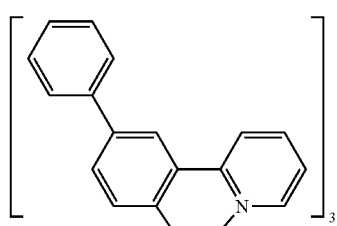
GD8
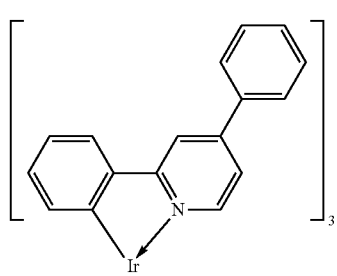
RD1
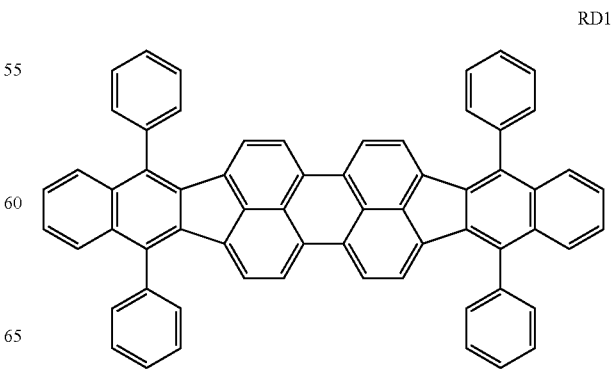

RD2
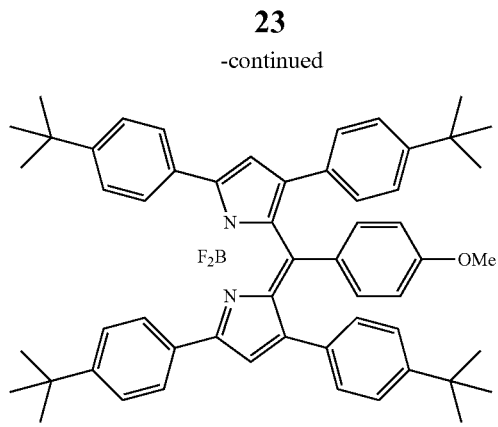

RD6
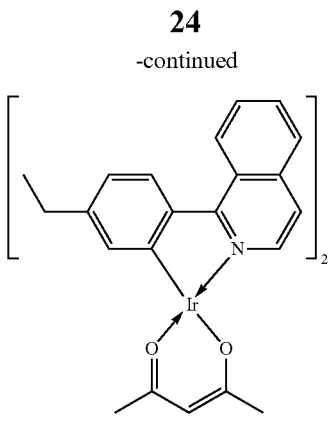

RD3
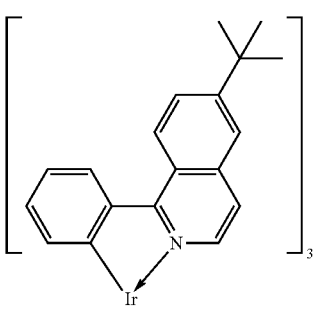

RD7
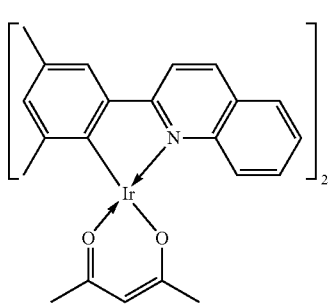

RD4
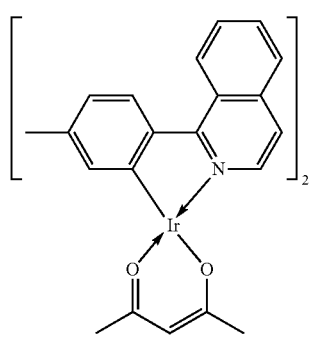

RD8
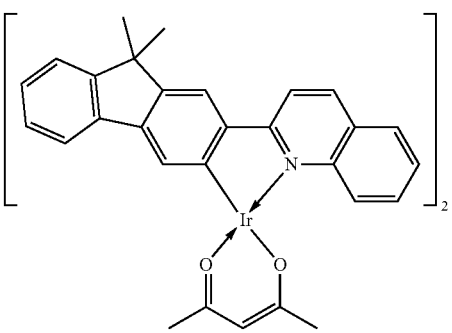

RD5
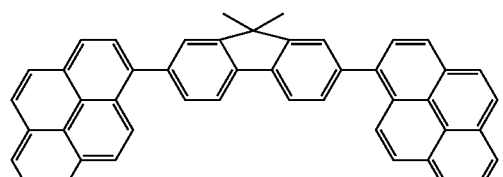

Examples of a host or an assist in the light-emitting layer include carbazole derivatives, dibenzofuran derivatives, dibenzothiophene derivatives, organoaluminum complexes such as tris(8-quinolinolato)aluminum, and organoberyllium complexes.

Compounds used as the host or the assist in the light-emitting layer are appropriately used also for the hole-blocking layer.

Non-limiting specific examples of a compound used as the host in the light-emitting layer will be illustrated below.

EM1

EM2

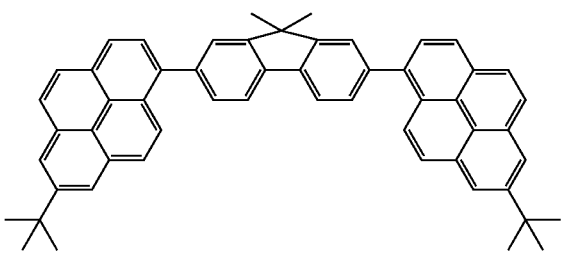

-continued
EM3
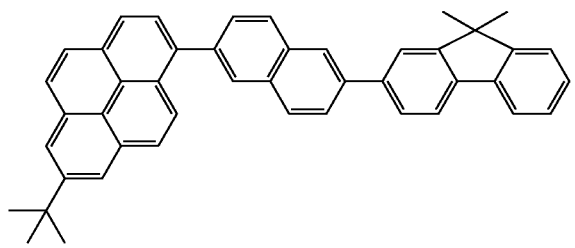
EM4
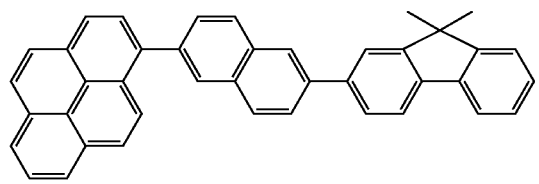
EM5
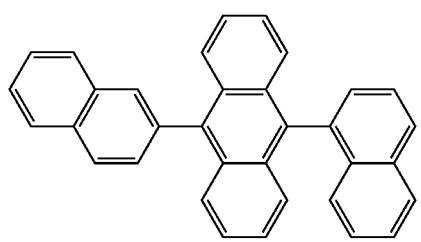
EM6
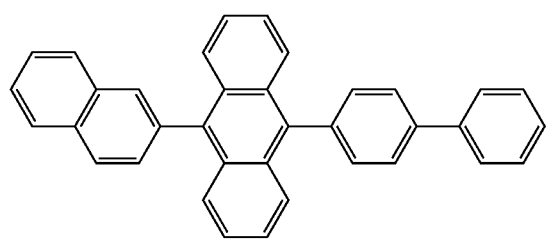
EM7
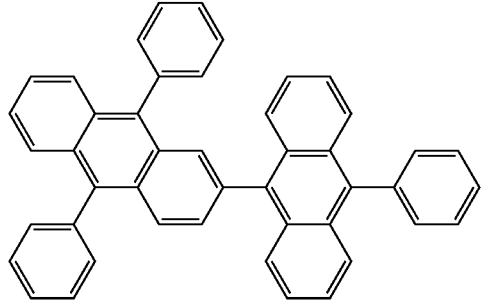
EM8
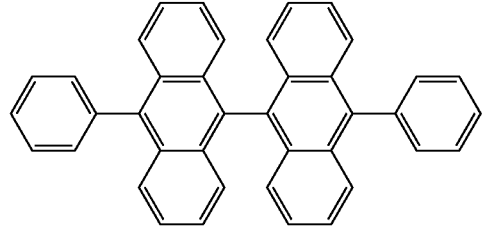
EM9
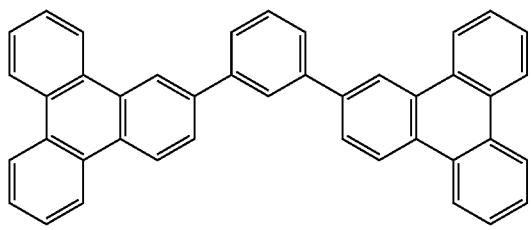
EM10
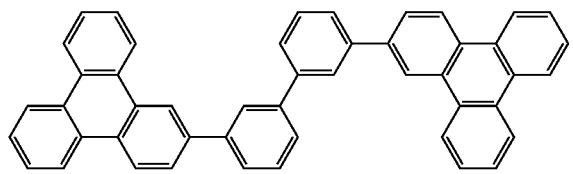
EM11
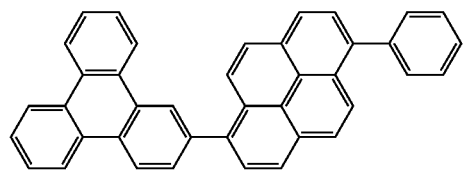
EM12
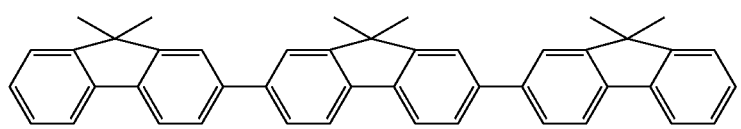
EM13
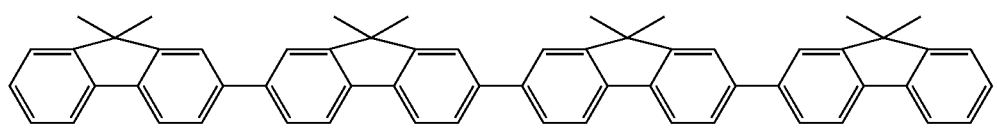

EM14
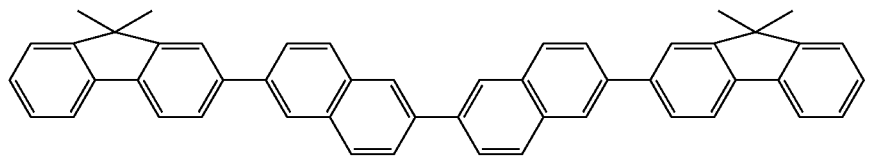
EM15 EM16
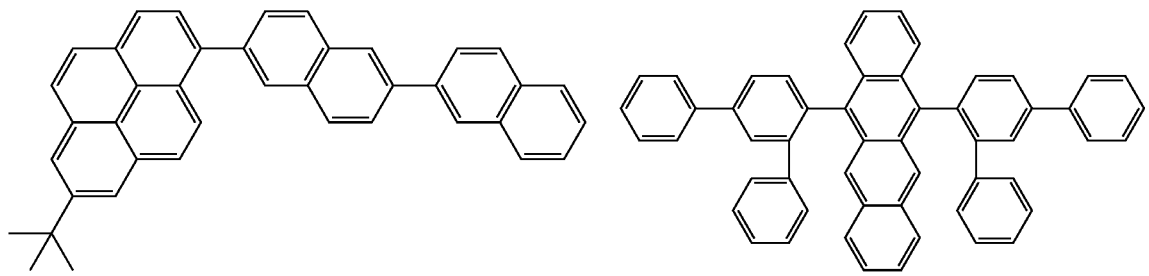
EM17 EM18
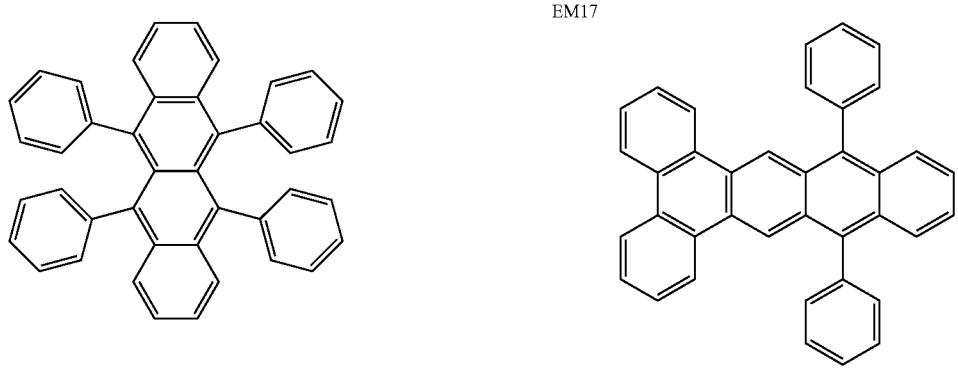
EM19 EM20
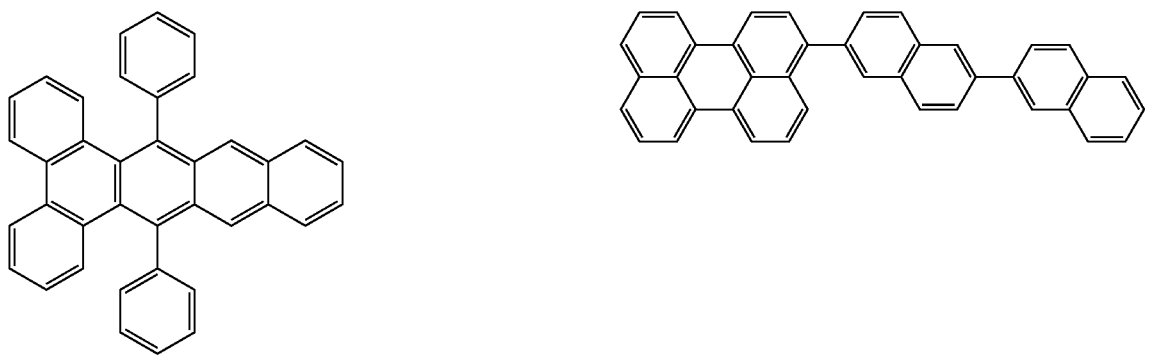
EM21 EM22
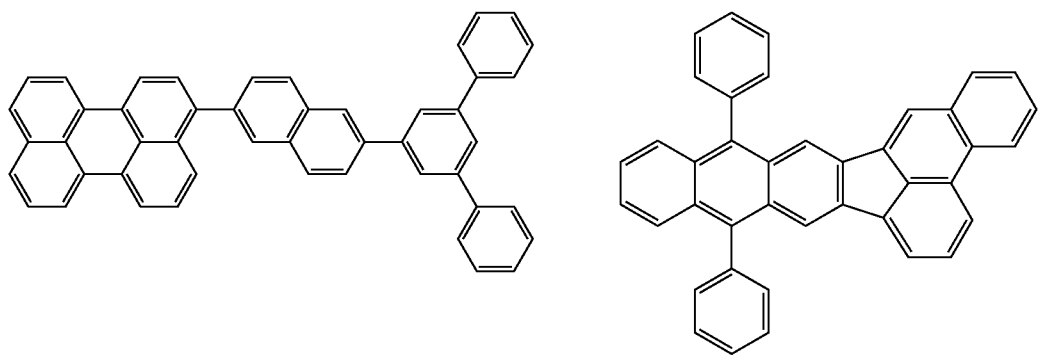

-continued
EM23
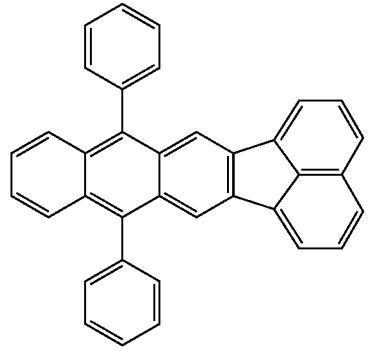
EM24
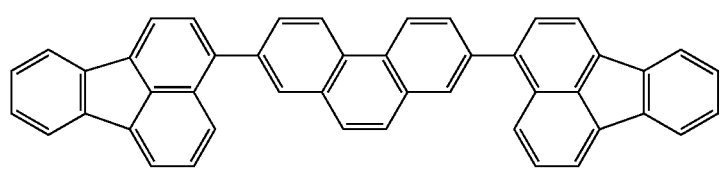
EM25
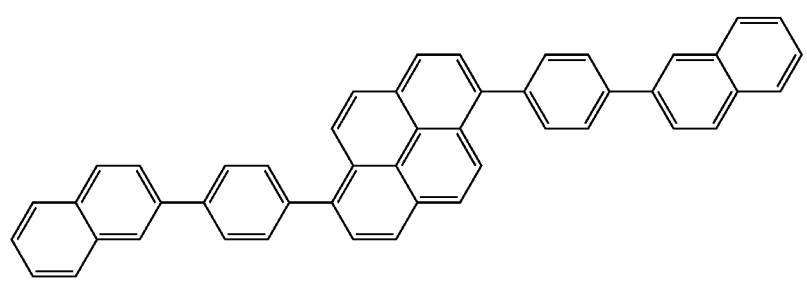
EM26
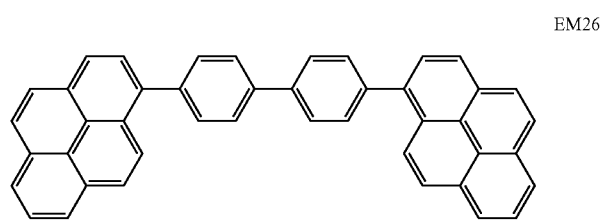
EM27
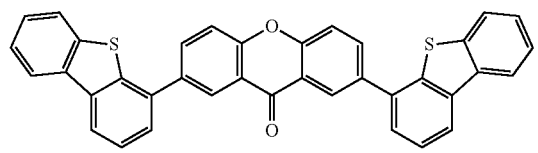
EM28
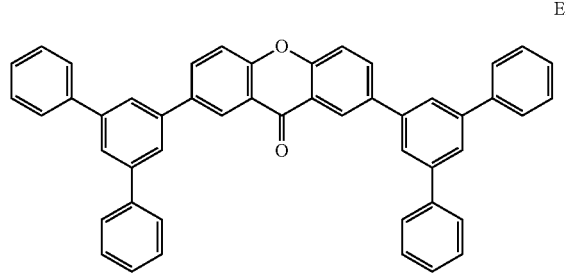
EM29
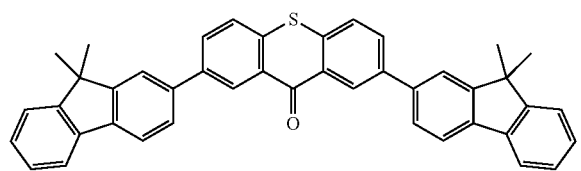
EM30
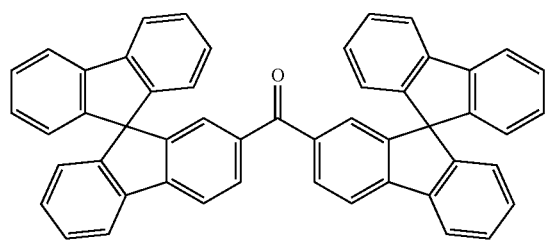
EM31
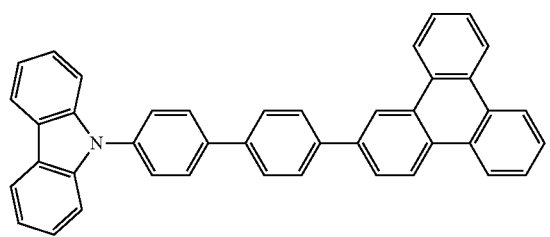

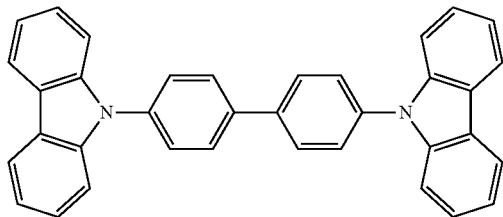

Among these, pyrene derivatives represented by EM1 to 4 can be used. In particular, EM1 or EM2 can be used.

The electron transport material can be freely-selected from materials capable of transporting electrons injected from the cathode to the light-emitting layer and is selected in consideration of, for example, the balance with the hole mobility of the hole transport material. Examples of a material having electron-transporting properties include oxadiazole derivatives, oxazole derivatives, pyrazine derivatives, triazole derivatives, triazine derivatives, quinoline derivatives, quinoxaline derivatives, phenanthroline derivatives, organoaluminum complexes, and condensed-ring compounds such as fluorene derivatives, naphthalene derivatives, chrysene derivatives, and anthracene derivatives. The electron transport materials are appropriately used for the hole-blocking layer. Non-limiting specific examples of a compound used as the electron transport material will be illustrated below.

ET1

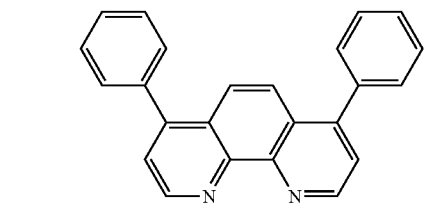

ET2

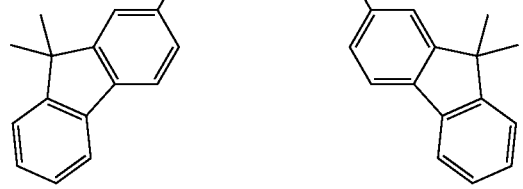

ET3

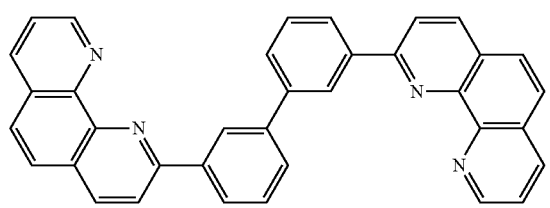

ET4

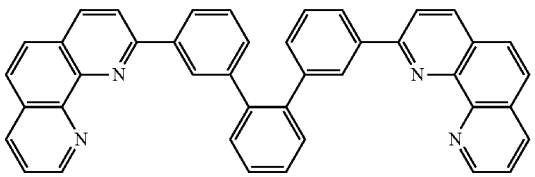

ET5

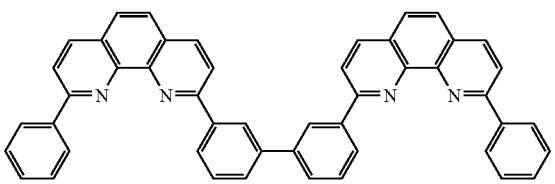

ET6

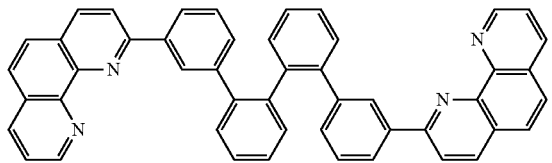

ET7

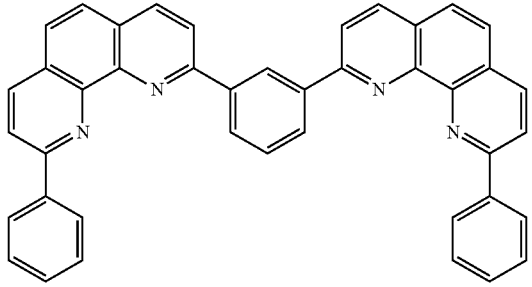

ET8

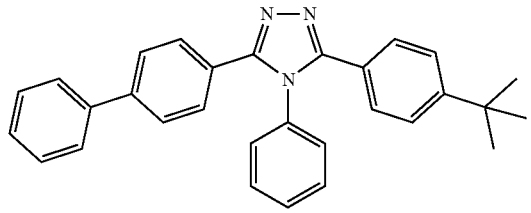

ET9
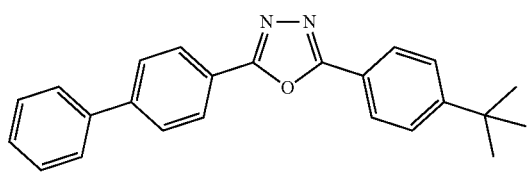
ET10
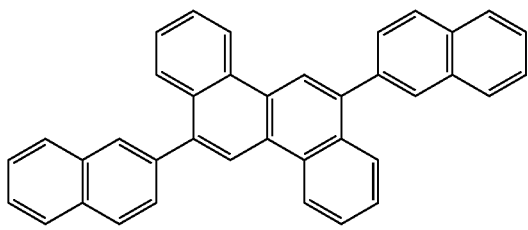
ET11
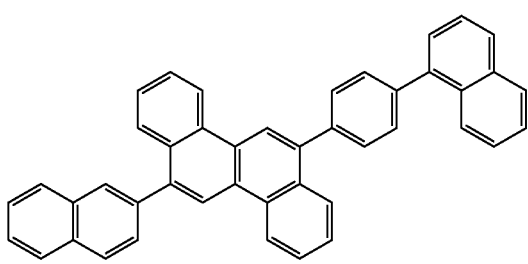
ET12
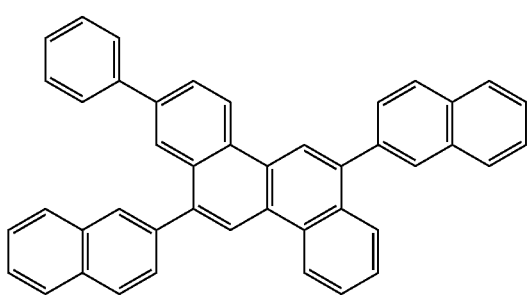
ET13
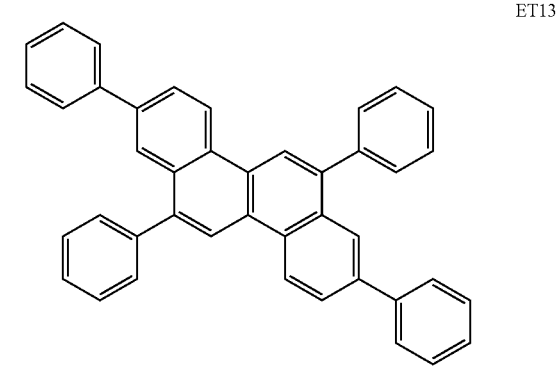
ET14
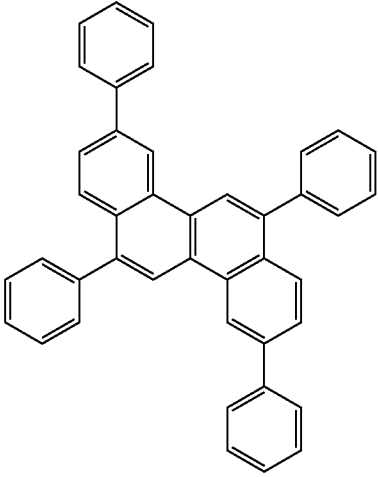
ET15
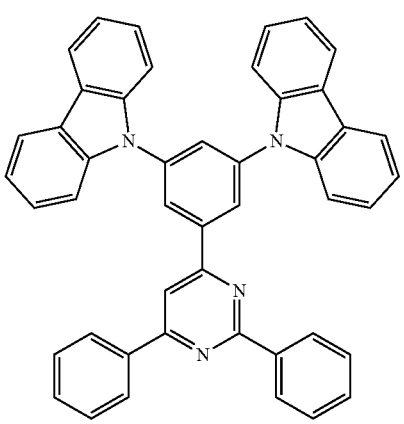
ET16
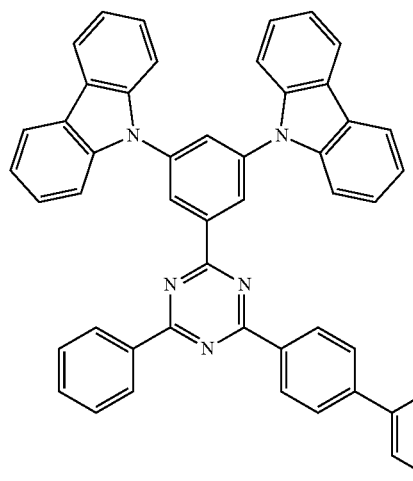

ET17
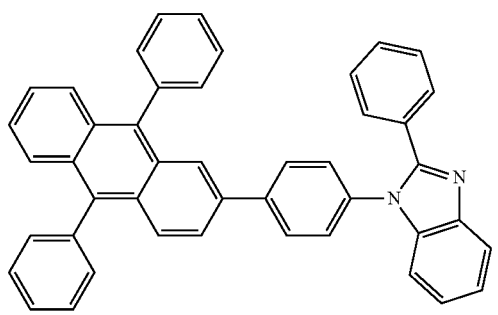

ET18
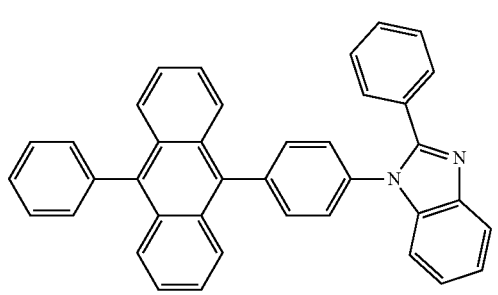

ET19
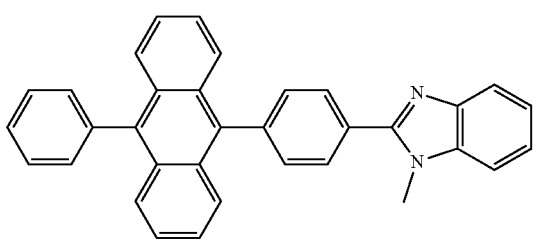

ET20
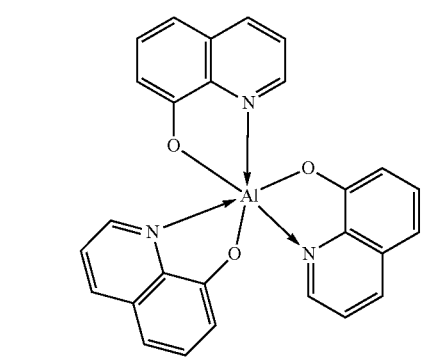

ET21
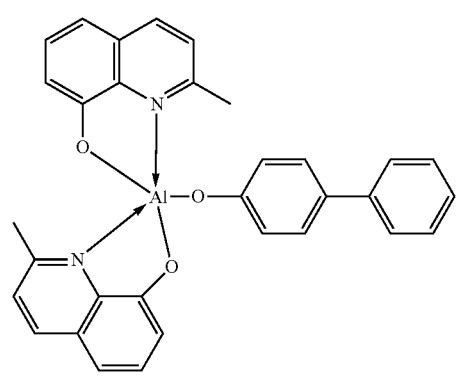

ET22
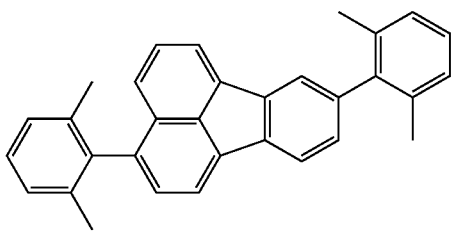

ET23
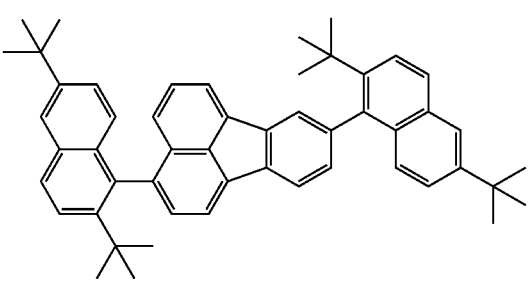

The electron injection material can be freely-selected from materials capable of easily injecting electrons from the cathode and is selected in consideration of, for example, the balance with the hole-injecting properties. The organic compounds include n-type dopants and reducing dopants. Examples thereof include alkali metal-containing compounds such as lithium fluoride, lithium complexes such as lithium quinolinolate, benzimidazolidene derivatives, imidazolidene derivatives, fulvalene derivatives, and acridine derivatives.

The organic light-emitting device is provided by disposing the anode, the organic compound layer, and the cathode on the substrate. A protective layer, a color filter, and so forth may be disposed on the cathode. In the case of disposing the color filter, a planarization layer may be disposed between the protective layer and the color filter. The planarization layer can be composed of, for example, an acrylic resin.

Examples of the substrate include silicon wafers, quartz substrates, glass substrates, resin substrates, and metal substrates. The substrate may include switching devices such as a transistor, a line, and an insulating layer thereon. As the insulating layer, any material can be used as long as a contact hole can be formed to establish the electrical connection between the anode and the line and as long as insulation with a non-connected line can be ensured. For example, a resin such as polyimide, silicon oxide, or silicon nitride can be used.

As the constituent material of the anode, a material having a work function as high as possible can be used. Examples of the material that can be used include elemental metals such as gold, platinum, silver, copper, nickel, palladium, cobalt, selenium, vanadium, and tungsten, mixtures thereof, alloys of combinations thereof, and metal oxides such as tin oxide, zinc oxide, indium oxide, indium-tin oxide (ITO), and indium-zinc oxide. Additionally, conductive polymers such as polyaniline, polypyrrole, and polythiophene may be used.

These electrode materials may be used alone or in combination of two or more. The anode may be formed of a single layer or multiple layers.

In the case where the anode is used as a reflective electrode, for example, chromium, aluminum, silver, titanium, tungsten, molybdenum, an alloy thereof, or a stack thereof may be used. In the case where the anode is used as a transparent electrode, a transparent conductive oxide layer composed of, for example, indium-tin oxide (ITO) or indium-zinc oxide may be used; however, the anode is not limited thereto. The electrode may be formed by photolithography.

As the constituent material of the cathode, a material having a lower work function can be used. Examples thereof include elemental metals such as alkali metals, e.g., lithium, alkaline-earth metals, e.g., calcium, aluminum, titanium, manganese, silver, lead, and chromium, and mixtures thereof Alloys of combinations thereof may also be used. For example, magnesium-silver, aluminum-lithium, aluminum-magnesium, silver-copper, and zinc-silver may be used. Metal oxides such as indium-tin oxide (ITO) may also be used. These electrode materials may be used alone or in combination of two or more. The cathode may have a single-layer structure or a multilayer structure. In particular, silver can be used. To reduce the aggregation of silver, a silver alloy can be used. Any alloy ratio may be used as long as the aggregation of silver can be reduced. For example, 1:1 may be used.

A top emission device may be provided using the cathode formed of a conductive oxide layer composed of, for example, ITO. A bottom emission device may be provided using the cathode formed of a reflective electrode composed of, for example, aluminum (Al). The cathode is not particularly limited. Any method for forming the cathode may be used. For example, a direct-current or alternating-current sputtering technique can be employed because good film coverage is obtained and thus the resistance is easily reduced.

After the formation of the cathode, a protective layer may be disposed. For example, a glass member provided with a moisture absorbent can be bonded to the cathode to reduce the entry of, for example, water into the organic compound layer to suppress the occurrence of display defects. In another embodiment, a passivation film composed of, for example, silicon nitride may be disposed on the cathode to reduce the entry of, for example, water into the organic compound layer and the cathode. For example, after the formation of the cathode, the substrate may be transported to another chamber without breaking the vacuum, and a silicon nitride film having a thickness of 2 may be formed by a chemical vapor deposition (CVD) method to provide a protective layer. After the film deposition by the CVD method, a protective layer may be formed by an atomic layer deposition (ALD) method.

A color filter may be provided for each pixel. For example, a color filter in accordance with the size of a pixel may be provided on another substrate and bonded to the substrate provided with the organic light-emitting device. A color filter may be formed by patterning on a protective film composed of, for example, silicon oxide using photolithography.

The organic compound layer (for example, the hole injection layer, the hole transport layer, the electron-blocking layer, the light-emitting layer, the hole-blocking layer, the electron transport layer, and the electron injection layer) included in the organic light-emitting device according to an embodiment of the present disclosure is formed by a method described below.

For the production of the organic compound layer, a dry process such as a vacuum evaporation method, an ionized evaporation method, sputtering, or plasma may be employed. Alternatively, instead of the dry process, it is also possible to employ a wet process in which a material is dissolved in an appropriate solvent and then a film is formed by a known coating method such as spin coating, dipping, a casting method, a Langmuir-Blodgett (LB) technique, or an ink jet method.

In the case where the layer is formed by, for example, the vacuum evaporation method or the solution coating method, crystallization is less likely to occur, and good stability with time is obtained. In the case of forming a film by the coating method, the film in combination with an appropriate binder resin may be formed.

Non-limiting examples of the binder resin include poly (vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

These binder resins may be used alone as a homopolymer or a copolymer or in combination as a mixture. Furthermore, additives such as a known plasticizer, antioxidant, and ultraviolet absorber may be used, as needed.

Application of Organic Light-Emitting Device According to the Embodiment

The organic light-emitting device according to the embodiment can be used as a component member of a display device or a lighting device. Other applications include exposure light sources for electrophotographic image forming apparatuses, backlights for liquid crystal displays, and light-emitting devices including white light sources and color filters.

The display device may be an image information-processing device having an image input unit that receives image information from an area or linear CCD sensor, a memory card, or any other source, an information-processing unit that processes the input information, and a display unit that displays the input image.

The display unit of an image pickup apparatus or an inkjet printer may have a touch-screen feature. The driving mode of the touch-screen feature may be, but is not limited to, an infrared mode, an electrostatic capacitive mode, a resistive film mode, or an electromagnetic inductive mode. The display device may also be used for a display unit of a multifunction printer.

The following describes a display device according to the embodiment with reference to the attached drawings. FIG. 1 is a schematic cross-sectional view illustrating an example of a display device including organic light-emitting devices and thin-film transistor (TFT) devices coupled to the organic light-emitting devices. The TFT devices are an example of active devices.

A display device 10 in FIG. 1 includes a substrate 11 composed of, for example, glass and an insulating layer 12 thereon, the insulating layer 12 being configured to protect the TFT devices or organic compound layers. The display device 10 includes the TFT devices 18 on the insulating layer 12. Each of the TFT devices includes a gate electrode 13, a gate insulating film 14 that covers the gate electrode 13, a semiconductor layer 15 that covers the gate insulating film, a drain electrode 16 in contact with the semiconductor layer 15, and a source electrode 17 in contact with the semiconductor layer 15 and different from the drain electrode 16. An insulating film 19 is disposed on the TFT devices 18. An anode 21 included in each organic light-emitting device 26 is coupled to the source electrode 17 through a contact hole 20.

The way of electric coupling between the electrodes (the anode and the cathode) included in the organic light-emitting device 26 and the electrodes (the source electrode and the drain electrode) included in the corresponding TFT device is not limited to the configuration illustrated in FIG.

1. It is sufficient that one of the anode and the cathode is electrically coupled to one of the source electrode and the drain electrode of the TFT device.

Although an organic compound layer 22 in the display device 10 in FIG. 1 is illustrated as a single layer; however, the organic compound layer 22 may be formed of multiple layers. A first protective layer 24 and a second protective layer 25 are disposed on a cathode 23 in order to reduce the deterioration of the organic light-emitting device.

In the display device 10 illustrated in FIG. 1, the transistors are used as switching elements; however, metal-insulator-metal (MIM) elements may be used as switching elements instead.

The transistors used in the display device 10 illustrated in FIG. 1 are not limited to transistors on a single-crystal silicon wafer and may be thin-film transistors having an active layer on the insulating surface of the substrate. Examples of the material of the active layer include single-crystal silicon, non-single-crystal silicon materials such as amorphous silicon and microcrystalline silicon, and non-single-crystal oxide semiconductors such as indium-zinc oxide and indium-gallium-zinc oxide. Thin-film transistors are also referred to as TFT devices.

The transistors in the display device 10 illustrated in FIG. 1 may be formed in the substrate such as a Si substrate. The expression "formed in the substrate" indicates that the transistors are produced by processing the substrate such as a Si substrate. In the case where the transistors are formed in the substrate, the substrate and the transistors can be deemed to be integrally formed.

In the organic light-emitting device according to the embodiment, the luminance is controlled by the TFT devices, which are an example of switching elements; thus, an image can be displayed at respective luminance levels by arranging multiple organic light-emitting devices in the plane. The switching elements according to the embodiment are not limited to the TFT devices and may be low-temperature polysilicon transistors or active-matrix drivers formed on a substrate such as a Si substrate. The expression "on a substrate" can also be said to be "in the substrate". Whether transistors are formed in the substrate or TFT devices are used is selected, depending on the size of a display unit. For example, when the display unit has a size of about 0.5 inches, organic light-emitting devices can be disposed on a Si substrate.

Figure 2:
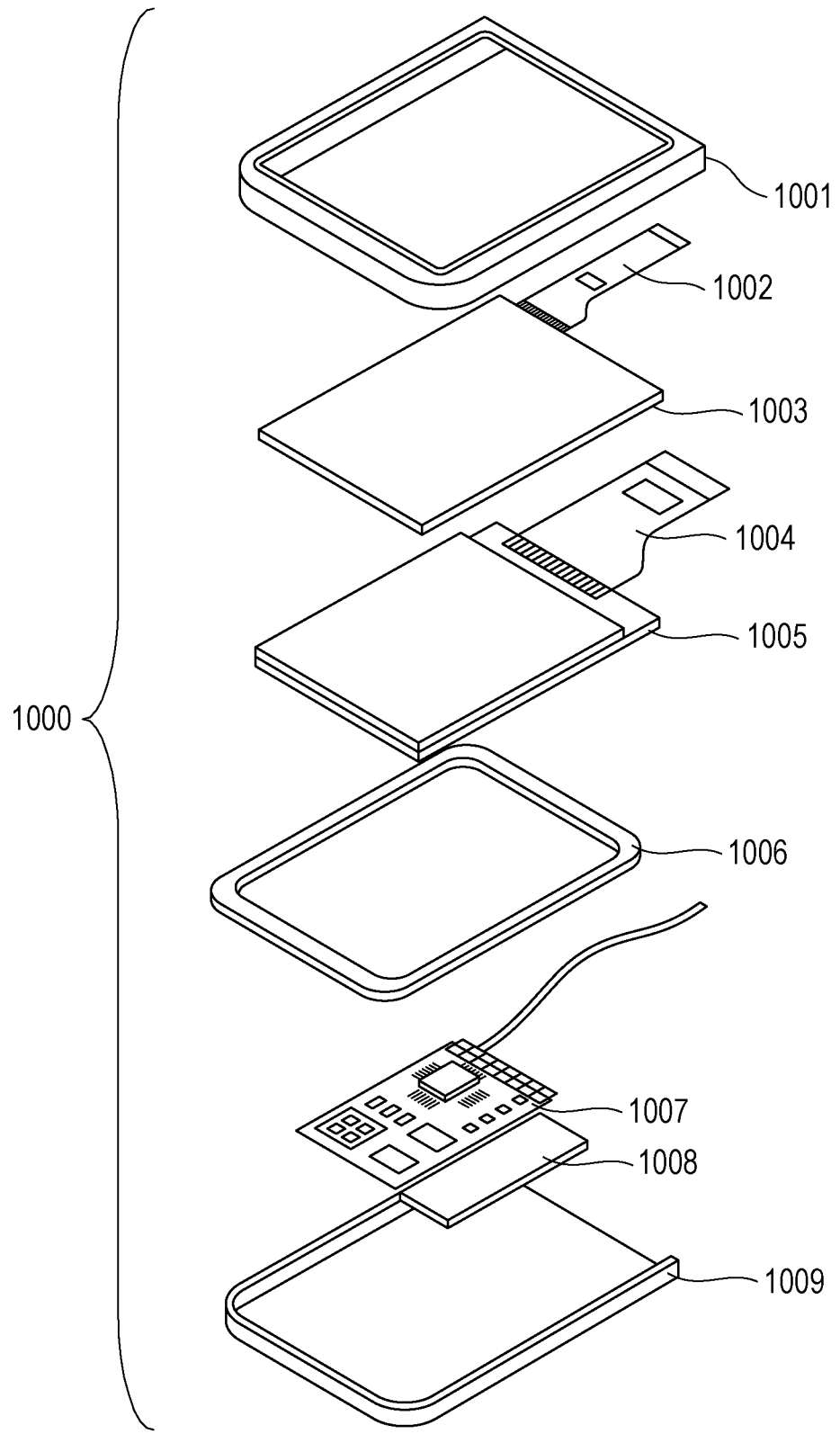
FIG. 2 is a schematic view illustrating an example of a display device according to an embodiment of the present disclosure.

FIG. 2 is a schematic view illustrating an example of a display device according to the embodiment. A display device 1000 may include a touch screen 1003, a display panel 1005, a frame 1006, a circuit substrate 1007, and a battery 1008 disposed between an upper cover 1001 and a lower cover 1009. The touch screen 1003 and the display panel 1005 are coupled to flexible printed circuits FPCs 1002 and 1004, respectively. The circuit substrate 1007 includes printed transistors. The battery 1008 need not be provided unless the display device is a portable device. The battery 1008 may be disposed at a different position even if the display device is a portable device.

The display device according to the embodiment may be used for a display unit of an image pickup apparatus including an optical unit including multiple lenses and an image pickup device that receives light passing through the optical unit. The image pickup apparatus may include a display unit that displays information acquired by the image pickup device. The display unit may be a display unit exposed to the outside of the image pickup apparatus or a display unit disposed in a finder. The image pickup apparatus may be a digital camera or a digital camcorder. The image pickup apparatus may translate to a photoelectric conversion apparatus. Examples of an image capturing method employed in the photoelectric conversion apparatus may include a method for detecting a difference from the previous image and a method of cutting out an image from images always recorded, instead of sequentially capturing images.

Figure 3A:
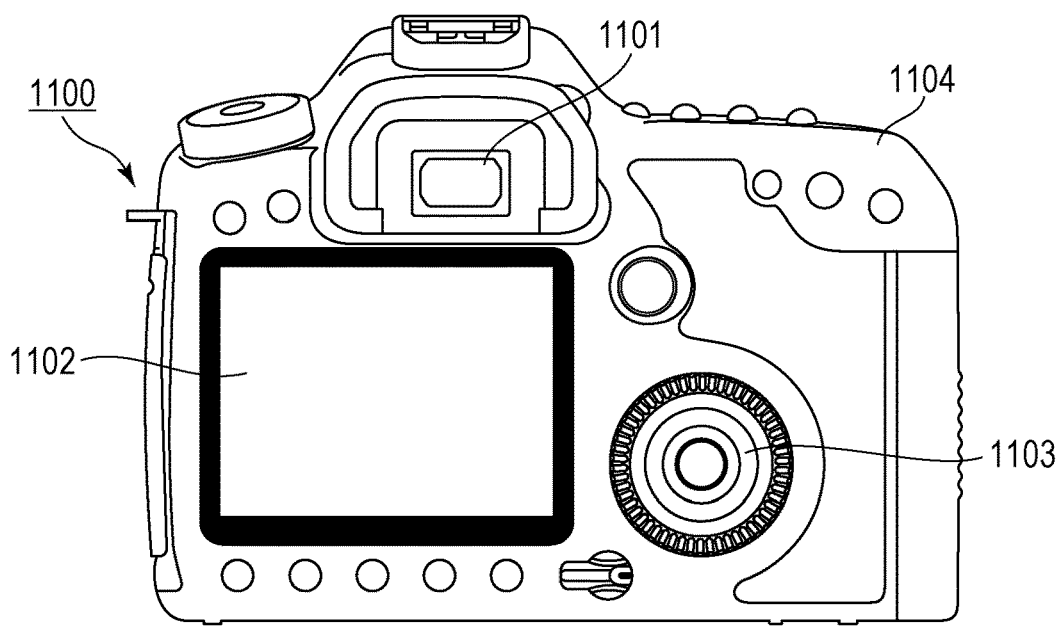
FIG. 3A is a schematic view illustrating an example of an image pickup apparatus according to an embodiment of the present disclosure.

FIG. 3A is a schematic view illustrating an example of an image pickup apparatus according to the embodiment. An image pickup apparatus 1100 may include a viewfinder 1101, a rear display 1102, an operation unit 1103, and a housing 1104. The viewfinder 1101 may include the display device according to the embodiment. In this case, the display device may display environmental information, imaging instructions, and so forth in addition to an image to be captured. The environmental information may include, for example, the intensity of external light, the direction of external light, the moving speed of a subject, and the possibility that a subject is shielded by a shielding material.

The timing suitable for imaging is only for a short time; thus, the information may be displayed as soon as possible. Accordingly, the display device including the organic light-emitting device according to an embodiment of the present disclosure can be used because of its short response time. The display device including the organic light-emitting device can be used more suitably than liquid crystal displays for these units required to have a high display speed.

The image pickup apparatus 1100 includes an optical unit (not illustrated). The optical unit includes multiple lenses and is configured to form an image on an image pickup device in the housing 1104. The relative positions of the multiple lenses can be adjusted to adjust the focal point. This operation can also be performed automatically.

The display device according to the embodiment may include a color filter having red, green, and blue pixels. In the color filter, the red, green, and blue pixels may be arranged in a delta arrangement.

The display device according to the embodiment may be used for the display unit of a portable terminal. In that case, the display device may have both a display function and an operation function. Examples of the portable terminal include mobile phones such as smartphones, tablets, and head-mounted displays.

Figure 3B:
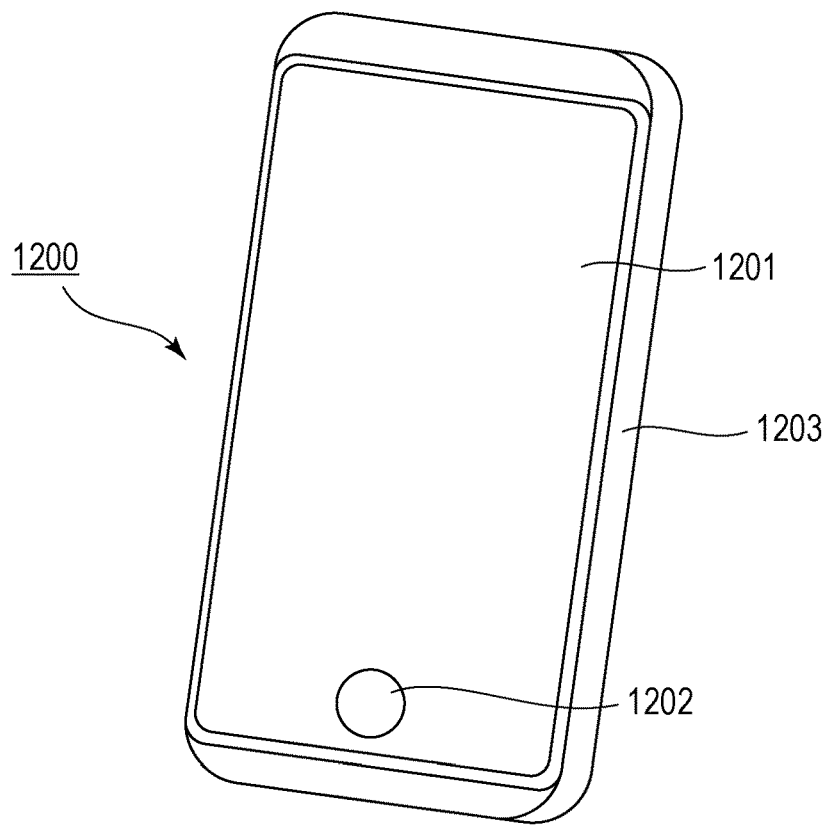
FIG. 3B is a schematic view illustrating an example of a portable apparatus according to an embodiment of the present disclosure.

FIG. 3B is a schematic view illustrating an example of an electronic apparatus according to the embodiment. An electronic apparatus 1200 includes a display unit 1201, an operation unit 1202, and a housing 1203. The housing 1203 may accommodate a circuit, a printed circuit board including the circuit, a battery, and a communication unit. The operation unit 1202 may be a button or a touch-screen-type reactive unit. The operation unit may be a biometric recognition unit that recognizes a fingerprint to release the lock or the like. An electronic apparatus having a communication unit can also be referred to as a communication apparatus.

Figure 4A:
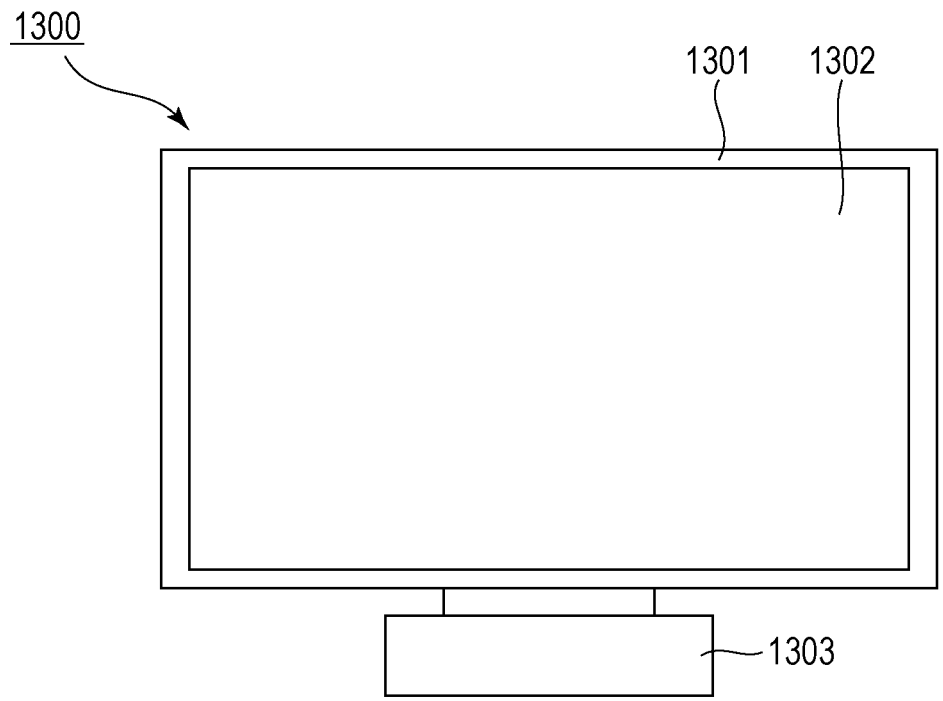
FIG. 4A is a schematic view illustrating an example of a display device according to an embodiment of the present disclosure.

FIG. 4A is a schematic view illustrating an example of the display device according to the embodiment. FIG. 4A illustrates a display device such as a television monitor or a PC monitor. A display device 1300 includes a frame 1301 and a display unit 1302. The light-emitting device according to the embodiment may be used for the display unit 1302.

A base 1303 that supports the frame 1301 and the display unit 1302 is provided. The base 1303 is not limited to the structure illustrated in FIG. 4A. The lower side of the frame 1301 may also serve as a base.

The frame 1301 and the display unit 1302 may be curved. These may have a radius of curvature of 5,000 mm or more and 6,000 mm or less.

Figure 4B:
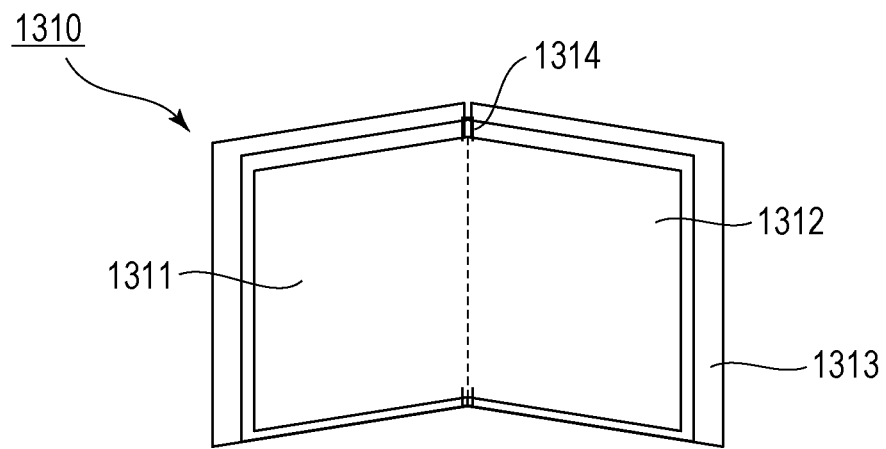
FIG. 4B is a schematic view illustrating an example of a foldable display device.

FIG. 4B is a schematic view illustrating another example of a display device according to the embodiment. A display device 1310 illustrated in FIG. 4B can be folded and is what is called a foldable display device. The display device 1310 includes a first display portion 1311, a second display portion 1312, a housing 1313, and an inflection point 1314. The first display portion 1311 and the second display portion 1312 may include the light-emitting device according to the embodiment. The first display portion 1311 and the second display portion 1312 may be a single, seamless display device. The first display portion 1311 and the second display portion 1312 can be divided from each other at the inflection point. The first display portion 1311 and the second display portion 1312 may display different images. Alternatively, a single image may be displayed in the first and second display portions.

Figure 5A:
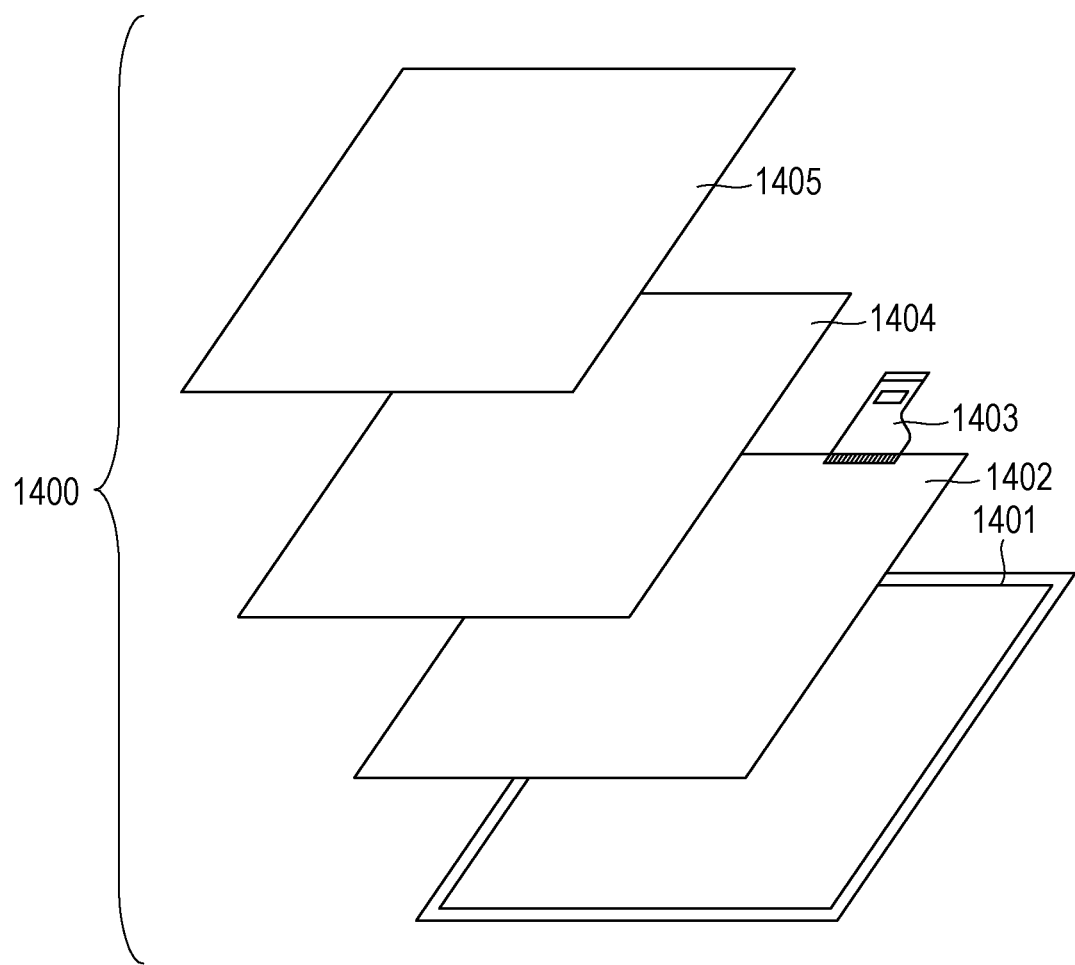
FIG. 5A is a schematic view illustrating an example of a lighting device according to an embodiment of the present disclosure.

FIG. 5A is a schematic view illustrating an example of a lighting device according to the embodiment. A lighting device 1400 may include a housing 1401, a light source 1402, a circuit board 1403, an optical film 1404, and a light diffusion unit 1405. The light source may include the organic light-emitting device according to the embodiment. The optical filter may be a filter that improves the color rendering properties of the light source. The light diffusion unit can effectively diffuse light from the light source to deliver the light to a wide range when used for illumination and so forth. The optical filter and the light diffusion unit may be disposed at the outgoing light side of the lighting device. A cover may be disposed at the outermost portion, as needed.

The lighting device is, for example, a device that lights a room. The lighting device may emit light of white, neutral white, or any color from blue to red. A light control circuit that controls the light may be provided. The lighting device may include the organic light-emitting device according to the embodiment of the present disclosure and a power supply circuit coupled thereto. The power supply circuit is a circuit that converts an AC voltage into a DC voltage. The color temperature of white is 4,200 K, and the color temperature of neutral white is 5,000 K. The lighting device may include a color filter.

The lighting device according to the embodiment may include a heat dissipation unit. The heat dissipation unit is configured to release heat in the device to the outside of the device and is composed of, for example, a metal having a high specific heat and liquid silicone.

Figure 5B:
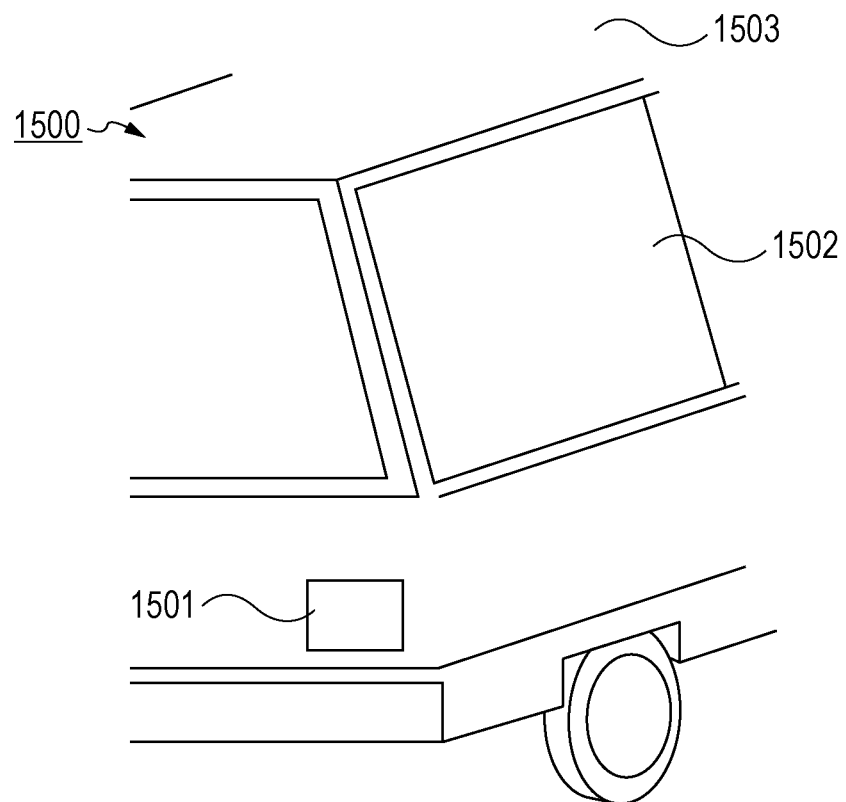
FIG. 5B is a schematic view illustrating an automobile as an example of a moving object according to an embodiment of the present disclosure.

FIG. 5B is a schematic view illustrating an automobile as an example of a moving object according to the embodiment. The automobile includes a tail lamp, which is an example of lamps. An automobile 1500 includes a tail lamp 1501 and may be configured to light the tail lamp when a brake operation or the like is performed.

The tail lamp 1501 may include the organic light-emitting device according to the embodiment. The tail lamp may include a protective member that protects the organic light-emitting device. The protective member may be composed of any transparent material having high strength to some extent and can be composed of, for example, polycarbonate. The polycarbonate may be mixed with, for example, a furandicarboxylic acid derivative or an acrylonitrile derivative.

The automobile 1500 may include an automobile body 1503 and windows 1502 attached thereto. The windows may be transparent displays if the windows are not used to check the front and back of the automobile. The transparent displays may include the organic light-emitting devices according to the embodiment. In this case, the components, such as the electrodes, of the organic light-emitting devices are formed of transparent members.

A moving object according to the embodiment may be, for example, a ship, an aircraft, or a drone. The moving object may include a body and a lamp attached to the body. The lamp may emit light to indicate the position of the body. The lamp includes the organic light-emitting device according to the embodiment.

As described above, when the device including the organic light-emitting device according to the embodiment is used, a stable display can be obtained with good image quality even for a long time display.

EXAMPLES

The present disclosure will be described below by examples. The present disclosure, however, is not limited thereto. Table 1 presents compounds contained in compositions according to an embodiment of the present disclosure. In Examples, anthracene compounds A to C are expressed as anthracene compounds, and each of the anthracene compounds is represented by formula [1] and has a hydrogen atom at at least one of positions 9 and 10.

TABLE 1

| Organic compound | Anthracene compound A | Anthracene compound B | Anthracene compound C |
|---|---|---|---|
| Composition 1 | [structure] | [structure] | [structure] | [structure] |

TABLE 1-continued

| | Organic compound | Anthracene compound A | Anthracene compound B | Anthracene compound C |
|---|---|---|---|---|
| Composition 2 | | | | |
| Composition 3 | | | | |
| Composition 4 | | | | |
| Composition 5 | | | | |
| Composition 6 | | | | |

TABLE 1-continued

| | Organic compound | Anthracene compound A | Anthracene compound B | Anthracene compound C |
|---|---|---|---|---|
| Composition 7 | 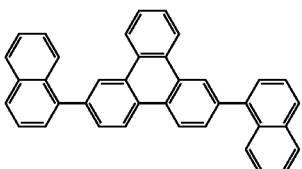 | 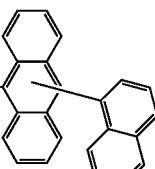 | 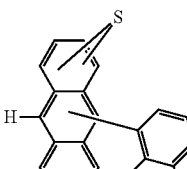 | 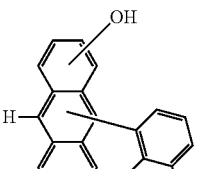 |

The concentration of each of anthracene compounds A to C in each composition of this example is 100 ppm or less. The total concentration of anthracene compounds A to C is preferably 100 ppm or less, more preferably 75 ppm or less, even more preferably 30 ppm. Each of anthracene compounds A to C has a hydrogen atom at at least one of positions 9 and 10 and is an example of the anthracene compound represented by formula [1]. Anthracene compound A is an anthracene compound consisting only of a hydrocarbon. Anthracene compound B is an anthracene compound having a chalcogen atom. Anthracene compound C is an anthracene compound having a hydroxy group. Anthracene compounds A to C are also referred to as impurities A to C.

Each of the naphthyl groups in compositions 1, 3, 5, and 7 in Table 1 may be attached at position 2. Each of the anthracene skeletons in composition 2 may further have a substituent at a position other than positions 9 or 10. Each of the biphenyl groups in composition 4 may be 9,9-dimethylfluorene. The phenanthryl group in composition 6 may further have a substituent.

Identification of Anthracene Compounds A to C Contained in Each Composition

Each of the compositions described in Table 1 contains the organic compound and anthracene compounds A to C represented by structural formulae. Anthracene compounds A to C were identified by analysis with a high-performance liquid chromatograph with a tandem mass spectrometer (LC/MS/MS).

The high-performance liquid chromatograph with a tandem mass spectrometer is an instrument in which a high-performance liquid chromatograph is directly connected to a tandem mass spectrometer that can perform MS/MS measurement. A mass-mass (MS/MS) method is a mode of mass spectrometry in which structural analysis of a sample can be easily performed by measuring fragments, obtained using a first analysis system, using a second analysis system to detect fragments having smaller molecular weights. In Examples, the high-performance liquid chromatograph coupled to a tandem mass spectrometer was used as an analyzer. As the high-performance liquid chromatograph, Agilent 1100 available from Agilent Technologies, Inc. was used. As a mass spectrometer, LTQ Orbitrap XL available from Thermofisher scientific was used.

The concentration of each of anthracene compounds A to C was measured by high-performance liquid chromatography, and the relative purity was calculated.

A measurement sample was provided by preparing a solution of 1 mg of a sample in 5 mL chloroform. Measurement was performed under conditions: absorption detector: 254 nm, emission detector: excitation wavelength: 354 nm, emission wavelength: 416 nm.

The relative purity of each of anthracene compounds A to C contained in compositions of Examples was determined by this method and found to be 0.01% or less=100 ppm or less.

Detection of Anthracene Compound A to C Contained in Organic Light-Emitting Device When anthracene compounds A to C are directly detected from the organic compound layer of the organic light-emitting device, unlike detection from the compositions, anthracene compounds A to C are contained in very small amounts and thus cannot be detected by high-performance liquid chromatography, in some cases. In such a case, an analysis method with higher sensitivity than the measurement method described above can be employed. There is an analysis method using a time-of-flight mass spectrometer (TOF-MS) as a measurement method suitable for this case. The concentration of each of anthracene compounds A to C contained in the compositions of Examples was determined by this method and found to be 10 ppm or less with respect to the organic compound contained in the organic light-emitting device.

Example 1

In this example, organic light-emitting devices having a structure presented in Table 2 were produced, each of the organic light-emitting devices having a bottom emission structure in which an anode, a hole transport layer, an electron-blocking layer, a light-emitting layer, a hole-blocking layer, an electron transport layer, an electron injection layer, and a cathode were sequentially formed on a substrate.

ITO films were formed on glass substrates and subjected to desired patterning to form ITO electrodes (anodes). Here, the thickness of each ITO electrode was 100 nm. Each substrate on which the ITO electrode had been formed in this way was used as an ITO substrate in the following steps. Next, resistance heating vacuum evaporation was performed in a vacuum chamber at a pressure of $1.33 \times 10^{-4}$ Pa to continuously form an organic compound layer and electrode layers presented in the following table on the ITO substrate. Here, the opposing electrode (metal electrode layer, cathode) had an electrode area of 3 mm². It is written that composition 1-1 was used as a host; however, the organic compound in composition 1 is intended to function as the host. That is, anthracene compounds A to C in the composition need not have the function of the host.

TABLE 2

| | Material | Film thickness (nm) |
|---|---|---|
| Anode | ITO | 100 |
| Hole transport layer | HT1 | 20 |
| Electron-blocking layer | HT8 | 10 |
| Light-emitting layer | host:composition 1-1 guest:BD6 composition:BD6 = 98:2 (ratio by weight) | 30 |
| Hole-blocking layer | ET22 | 10 |
| Electron transport layer | ET2 | 30 |
| Electron injection layer | LiF | 1 |
| Cathode | Al | 100 |

The characteristics of the resulting devices were measured and evaluated. Each of the light-emitting devices had a maximum emission wavelength of 450 nm and emitted blue light whose chromaticity coordinates (X, Y)=(0.14, 0.18).

The composition 1-1 in the light-emitting layer is composition 1, which is described in Table 1, having a composition ratio described in Table 3. A, B, and C in the table indicate anthracene compound A, anthracene compound B, and anthracene compound C, respectively. The composition ratios in the table are given in units of ppm. Table 3 presents the composition ratios of the compositions and the evaluation results of durability of the organic light-emitting devices containing the compositions. Composition 1-2 in the table is composition 1 different from composition 1-1 only in the composition ratio. The same applies to composition 1-3. The expression "N.D." in the table indicates that the concentration of the compound is less than the measurement limit. The measurement limit value in this example is less than 5 ppm. The expression "N.D." in other examples has the same meaning.

Table 3 presents the evaluation results of durability of the organic light-emitting devices produced in this example. The durability of each device was evaluated by a luminance half-life when the device was continuously driven while the current density was maintained at 100 mA/cm$^2$. A device having a luminance half-life of 1,000 hours or more is described as "AAA". A device having a luminance half-life of less than 1,000 hours and 500 hours or more is described as "AA". A device having a luminance half-life of less than 500 hours and 200 hours or more is described as "A". A device having a luminance half-life of less than 200 hours and 50 hours or more is described as "B". A device having a luminance half-life of less than 50 hours is described as "C".

TABLE 3

| | Composition | Concentration of anthracene compound A to C in composition 1 (ppm) | | | Durability evaluation result of device at 100 mA/cm$^2$ |
|---|---|---|---|---|---|
| | | A | B | C | |
| Example 1 | 1-1 | 20 | 70 | N.D. | A |
| | 1-2 | 10 | 10 | N.D. | AAA |
| Comparative example 1 | 1-2 | 150 | 120 | N.D. | C |

Examples 2 to 5

Organic light-emitting devices were produced in the same manner as in Example 1, except that compositions presented in Table 4 were appropriately used as the hosts. The characteristics of the resulting devices were measured and evaluated in the same manner as in Example 1. Table 4 presents the measurement results. As in Example 1, composition 3-2 is a composition different from composition 3-1 only in the composition ratio.

TABLE 4

| | Composition | Concentration of anthracene compound A to C in composition (ppm) | | | Durability evaluation result of device at 100 mA/cm$^2$ |
|---|---|---|---|---|---|
| | | A | B | C | |
| Example 2 | 3-1 | N.D. | 80 | N.D. | A |
| Comparative example 2 | 3-2 | N.D. | 250 | N.D. | C |
| Example 3 | 5-1 | 20 | 50 | N.D. | A |
| Comparative example 3 | 5-2 | 500 | 200 | N.D. | C |
| Example 4 | 6-1 | N.D. | 20 | 50 | AA |
| Comparative example 4 | 6-2 | N.D. | 170 | 450 | C |
| Example 5 | 7-1 | 20 | 50 | 20 | A |
| Comparative example 5 | 7-2 | 120 | 200 | 150 | C |

Examples 6 and 7

In these examples, organic light-emitting devices having a structure presented in Table 5 were produced, each of the organic light-emitting devices having a top emission structure in which an anode, a hole injection layer, a hole transport layer, an electron-blocking layer, a first light-emitting layer, a second light-emitting layer, hole-blocking layer, an electron transport layer, an electron injection layer, and a cathode were sequentially formed on a substrate.

Laminated films of Al and Ti having a thickness of 40 nm were formed on glass substrate by a sputtering method and patterned using photolithography to form anodes. Here, the opposing electrode (metal electrode layer, cathode) had an electrode area of 3 mm$^2$. Each cleaned substrate including the electrode and materials were placed in a vacuum evaporation apparatus. After the apparatus was evacuated to a pressure of $1.33\times10^{-4}$ Pa ($1\times10^{-6}$ Torr), UV/ozone cleaning was performed. The layers were formed in such a manner that a layer structure presented in Table 5 was achieved. Sealing was performed in a nitrogen atmosphere.

TABLE 5

| | Material | Film thickness (nm) |
|---|---|---|
| Hole injection layer | HT16 | 5 |
| Hole transport layer | HT2 | 20 |
| Electron-blocking layer | HT7 | 10 |
| First light-emitting layer | host: composition described in Table 6 guest:BD7 (composition:BD7 = 99.5:0.5 (ratio by weight)) | 10 |
| Second light-emitting layer | host: composition described in Table 6 guest 1:RD1 guest 2:GD4 (composition:RD1:GD4 = 97.7:0.3:2 (ratio by weight)) | 10 |

TABLE 5-continued

| | Material | Film thickness (nm) |
|---|---|---|
| Hole-blocking layer | ET23 | 80 |
| Electron transport layer | ET3 | 30 |
| Electron injection layer | LiF | 1 |
| Cathode | Mg:Ag = 50:50 (ratio by weight) | 10 |

The characteristics of the resulting devices were measured and evaluated. Each device emitted white light whose chromaticity coordinates (X, Y)=(0.31, 0.33). Table 6 presents the evaluation results of durability of the organic light-emitting devices produced in these examples. The durability of each device was evaluated by a luminance half-life when the device was continuously driven while the current density was maintained at 100 mA/cm$^2$. A device having a luminance half-life of 2,000 hours or more is described as "AAA". A device having a luminance half-life of less than 2,000 hours and 1,500 hours or more is described as "AA". A device having a luminance half-life of less than 1,500 hours and 1,000 hours or more is described as "A". A device having a luminance half-life of less than 1,000 hours and 500 hours or more is described as "B". A device having a luminance half-life of less than 500 hours is described as "C".

TABLE 6

| | Composition | Concentration of anthracene compound A to C in composition (ppm) | | | Durability evaluation result of device |
|---|---|---|---|---|---|
| | | A | B | C | at 100 mA/cm$^2$ |
| Example 6 | 2-1 | 10 | 50 | 20 | A |
| | 2-2 | 10 | 20 | 20 | AA |
| Comparative example 6 | 2-3 | 150 | 350 | 120 | C |
| Example 7 | 4-1 | N.D. | 70 | N.D. | A |
| | 4-2 | N.D. | 20 | N.D. | AAA |
| Comparative example 7 | 4-3 | N.D. | 170 | N.D. | C |

Examples 8 and 9

Organic light-emitting devices were produced in the same manner as in Example 6, except that compositions presented in Table 7 were appropriately used as materials of the hole-blocking layers.

TABLE 7

| | Material | Film thickness (nm) |
|---|---|---|
| Hole injection layer | HT16 | 5 |
| Hole transport layer | HT2 | 20 |
| Electron-blocking layer | HT7 | 10 |
| First light-emitting layer | host:composition 2-1 guest:BD7 (composition 2-1:BD7 = 99.5:0.5 (ratio by weight)) | 10 |
| Second light-emitting layer | host: composition 2-1 guest 1:RD1 guest 2:GD4 (composition 2-1:RD1:GD4 = 97.7:0.3:2 (ratio by weight)) | 10 |

TABLE 7-continued

| | Material | Film thickness (nm) |
|---|---|---|
| Hole-blocking layer | composition described in Table 8 | 80 |
| Electron transport layer | ET3 | 30 |
| Electron injection layer | LiF | 1 |
| Cathode | Mg:Ag = 50:50 (ratio by weight) | 10 |

The characteristics of the resulting devices were measured and evaluated in the same manner as in Example 6. Table 8 presents the measurement results. The notation of the evaluation results of durability of the devices in Table 8 is the same as used in Tables 3 and 6.

TABLE 8

| | Composition | Concentration of anthracene compound A to C in composition (ppm) | | | Durability evaluation result of device |
|---|---|---|---|---|---|
| | | A | B | C | at 100 mA/cm$^2$ |
| Example 8 | 1-1 | 20 | 70 | N.D. | A |
| Comparative example 8 | 1-3 | 150 | 120 | N.D. | B |
| Example 9 | 5-1 | 20 | 50 | N.D. | A |
| Comparative example 9 | 5-2 | 500 | 200 | N.D. | B |

The foregoing assessment results indicate that when the composition containing reduced concentrations of the highly active anthracene compounds represented by formula [1] is used for the light-emitting layer and the hole-blocking layer adjacent to the light-emitting layer, the driving lifetime of the organic light-emitting device can be improved. In particular, the reduction of anthracene compound B is significantly effective in improving the driving lifetime of the organic light-emitting device.

Methods for reducing anthracene compounds A to C will be specifically described below.

Example 10

Compounds, a reagent, and a solvent described below were placed into a 300-mL round bottomed flask.
Composition 1-3 (A: 150 ppm, B: 120 ppm, C: N.D.): 2 g (4.0 mmol)
Maleic anhydride: 0.78 g (8.0 mmol)
Dehydrated xylene: 200 mL Note that A, B, and C in composition 1-3 are anthracene compounds A, B, and C, respectively.

The reaction solution was heated to 145° C. under a stream of nitrogen and stirred for 3 hours under reflux. After the completion of the reaction, the mixture was cooled to room temperature and filtered to give a crude filtered product. The resulting filtered product, a reagent, and a solvent described below were placed in a 300-mL round bottomed flask, and then post treatment and purification were performed.
Alumina: 20 g
Chlorobenzene: 150 mL The mixture was heated and stirred at 80° C. for 1 hour and then hot-filtered at this temperature. The resulting filtrate was concentrated to about 60 mL and then heated to 110° C. to dissolve crude crystals. Recrystallization was performed by slowly cooling the solution to room temperature and then 10° C. or lower. The resulting crystals were filtered. The crystals were subjected to slurry washing with two 20-mL portions of toluene at room temperature. The resulting crystals were subjected to drying and sublimation purification to give 1.4 g (yield: 70%) of composition 1-1. Composition 1-1 was measured by high-performance liquid chromatography. The calculation of the relative purities of anthracene compounds A and B with respect to 9,10-di(naphthalen-1-yl)-2-phenylanthracene indicated that the concentration of anthracene compounds A and the concentration of anthracene compound B were reduced to 20 ppm and 70 ppm, respectively.

In addition to the foregoing reaction, composition 1-1 thus obtained was subjected to sublimation purification to give 1.1 g (yield: 75%) of composition 1-2. The calculation of the relative purities of A and B by high-performance liquid chromatography in the same manner as above indicated that in composition 1-2, the concentration of each of anthracene compounds A and B was further reduced to 10 ppm.

Compositions 5-2, 6-2, 7-2, 2-3, and 4-1 were similarly treated by the method described in Example 10 to provide compositions 5-1, 6-1, 7-1, 2-1, and 4-2.

Comparative Example 10

First, 1 g (2 mmol) of Composition 1-3 (A: 150 ppm, B: 120 ppm, C: N.D.) was subject to only sublimation purification to give 0.8 g (yield: 80%) of the composition 1-3. The calculation of the relative purities of A and B to 9,10-di(naphthalen-1-yl)-2-phenylanthracene by high-performance liquid chromatography in the same manner as above indicated. No change was seen between the concentration of the relative purities of A and B after sublimation purification and the concentration of the relative purities of A and B before sublimation purification.

Example 11

Compounds, a reagent, and a solvent described below were placed into a 500-mL round bottomed flask.
Composition 3-2 (A: N.D., B: 250 ppm, C: N.D.): 2 g (4.4 mmol)
mCPBA: 0.23 g (1.3 mmol)
Chlorobenzene: 200 mL The reaction solution was heated to 50° C. under a stream of nitrogen and stirred for 3 hours. After the completion of the reaction, the mixture was cooled to room temperature and filtered to give a crude filtered product.

The resulting filtered product, a reagent, and a solvent described below were placed in a 300-mL round bottomed flask, and then post treatment and purification were performed.
Alumina: 20 g
Chlorobenzene: 300 mL The mixture was heated and stirred at 60° C. for 1 hour and then hot-filtered at this temperature. The resulting filtrate was concentrated to about 60 mL and then heated to 110° C. to dissolve crude crystals. Recrystallization was performed by slowly cooling the solution to room temperature and then 10° C. or lower. The resulting crystals were filtered. The crystals were subjected to slurry washing with two 20-mL portions of toluene at room temperature. The resulting crystals were subjected to drying and sublimation purification to give 1.2 g (yield: 60%) of composition 3-1. Composition 3-1 was measured by high-performance liquid chromatography. The calculation of the relative purity of anthracene compound B with respect to 1,6-di(naphthalen-1-yl)pyrene indicated that the concentration of anthracene compound B was reduced to 80 ppm.

Compositions 2-1 and 4-3 were similarly treated by the method described in Example 11 to provide compositions 2-2 and 4-1.

As described above, the compositions containing reduced concentrations of highly active anthracene compounds (A to C) represented by formula [1] were obtained by the Diels-Alder reaction, which is a selective addition reaction, or the oxidation reaction with mCPBA, which is a peroxide.

Comparative Example 11

First, 0.5 g (1.1 mmol) of Composition 3-2 (A: N.D., B: 250 ppm, C: N.D.) was subject to only sublimation purification to give 0.35 g (yield: 70%) of the composition 3-2. The calculation of the relative purities of A and B to 9,10-di(naphthalen-1-yl)-2-phenylanthracene by high-performance liquid chromatography in the same manner as above indicated. No change was seen between the concentration of the relative purities of A and B after sublimation purification and the concentration of the relative purities of A and B before sublimation purification. Other compositions have the same result.

According to the present disclosure, by the use of the composition containing reduced concentrations of the highly active compounds for the organic light-emitting device, the long-lived, stable organic light-emitting device can be provided.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A method for producing a composition, the composition containing an organic compound which is capable of emitting light and containing one or more kinds of anthracene compounds different from the organic compound, the one or more kinds of anthracene compounds each having a hydrogen atom at at least one of positions 9 and 10, the method comprising a step of:
reducing a content of the one or more kinds of anthracene compounds,
wherein the reducing is repeated until a total concentration of the one or more kinds of anthracene compounds is 50 ppm or less.

2. The method for producing a composition according to claim 1,
wherein the reducing is selectively reacting the one or more kinds of anthracene compounds by an addition reaction or an oxidation reaction.

3. The method for producing a composition according to claim 2,
wherein the addition reaction is a Diels-Alder reaction.

4. The method for producing a composition according to claim 2, wherein the oxidation reaction is an oxidation reaction using a peroxide.

5. The method for producing a composition according to claim 1,
wherein the total concentration of one or more kinds of anthracene compounds is 10 ppm or less.

6. The method for producing a composition according to claim 1,
  wherein each concentration of the one or more kinds of anthracene compounds is 20 ppm or less.

7. The method for producing a composition according to claim 1,
  wherein at least one of the one or more kinds of anthracene compounds is represented by formula [1]:

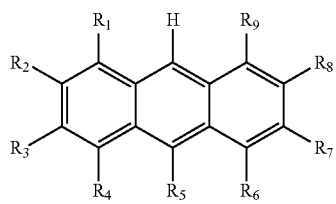

[1]

where in formula [1], $R_1$ to $R_9$ are each independently selected from the group consisting of a hydrogen atom, a chalcogen atom, a substituted or unsubstituted alkyl group, a substituted or unsubstituted aryl group, and a substituted or unsubstituted heterocyclic group, at least one of $R_1$ to $R_9$ is a substituted or unsubstituted aryl group, and adjacent substituents in $R_1$ to $R_9$ may be bonded to each other to form a ring.

8. The method for producing a composition according to claim 1,
  wherein the organic compound is a polycyclic aromatic hydrocarbon.

9. The method for producing a composition according to claim 8,
  wherein the organic compound is represented by any of formulae [2] to [6]:

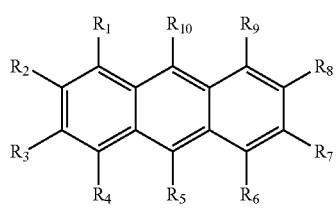

[2]

where in formula [2], $R_1$ to $R_{10}$ are substituents each independently selected from the group consisting of a hydrogen atom, a substituted or unsubstituted alkyl group, a substituted or unsubstituted aryl group, and a substituted or unsubstituted heterocyclic group, provided that at least one of $R_1$ to $R_9$ is a substituted or unsubstituted aryl group and that neither $R_5$ nor $R_{10}$ is a hydrogen atom,

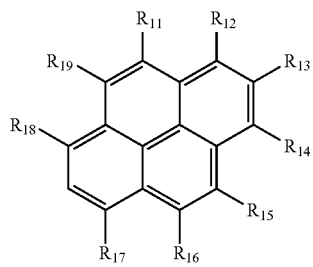

[3]

where in formula [3], $R_{11}$ to $R_{19}$ are substituents each independently selected from the group consisting of a hydrogen atom, a substituted or unsubstituted alkyl group, a substituted or unsubstituted aryl group, and a substituted or unsubstituted heterocyclic group,

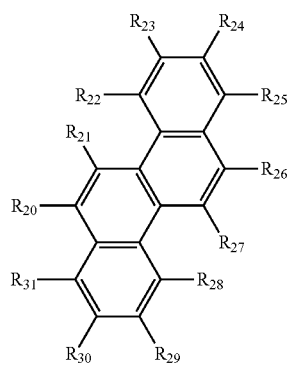

[4]

where in formula [4], $R_{20}$ to $R_{31}$ are substituents each independently selected from the group consisting of a hydrogen atom, a substituted or unsubstituted alkyl group, a substituted or unsubstituted aryl group, and a substituted or unsubstituted heterocyclic group,

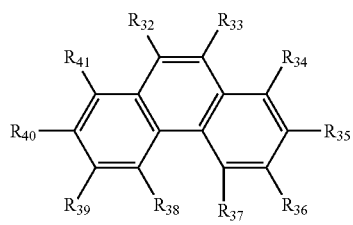

[5]

where in formula [5], $R_{32}$ to $R_{41}$ are substituents each independently selected from the group consisting of a hydrogen atom, a substituted or unsubstituted alkyl group, a substituted or unsubstituted aryl group, and a substituted or unsubstituted heterocyclic group, provided that at least one of $R_{32}$ to $R_{41}$ is a substituted or unsubstituted aryl group, and

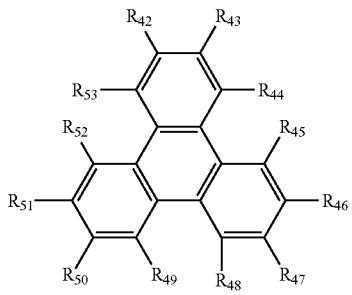

where in formula [6], $R_{42}$ to $R_{53}$ are substituents each independently selected from the group consisting of a hydrogen atom, a substituted or unsubstituted alkyl group, a substituted or unsubstituted aryl group, and a substituted or unsubstituted heterocyclic group.

10. The method for producing a composition according to claim 7,
wherein the organic compound is an anthracene derivative having a substituent other than a hydrogen atom at each of positions 9 and 10 or a pyrene derivative.

11. The method for producing a composition according to claim 7,
wherein in formula [1], at least one of $R_1$ to $R_9$ is a chalcogen atom.

12. The method for producing a composition according to claim 11,
wherein the chalcogen atom is a sulfur atom.

13. A method for manufacturing an organic light-emitting device, comprising:
forming an anode;
forming an organic compound layer above the anode by a vacuum evaporation method; and
forming a cathode above the organic compound layer,
wherein the organic compound layer includes the composition according to claim 1.

14. A method for producing a composition, the composition containing an organic compound which is capable of emitting light and containing one or more kinds of anthracene compounds different from the organic compound, the one or more kinds of anthracene compounds each having a hydrogen atom at at least one of positions 9 and 10, the method comprising a step of:
reducing the content of the one or more kinds of anthracene compounds,
wherein the reducing is repeated until a total concentration of the one or more kinds of anthracene compounds is 100 ppm or less, and
wherein at least one of the one or more kinds of anthracene compounds is represented by formula [1]:

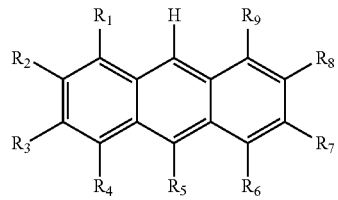

where in formula [1], $R_1$ to $R_9$ are each independently selected from the group consisting of a hydrogen atom, a chalcogen atom, a substituted or unsubstituted alkyl group, a substituted or unsubstituted aryl group, and a substituted or unsubstituted heterocyclic group, at least one of $R_1$ to $R_9$ is a substituted or unsubstituted aryl group, and adjacent substituents in $R_1$ to $R_9$ may be bonded to each other to form a ring.

15. A method for producing a composition, the composition containing an organic compound which is capable of emitting light and containing one or more kinds of anthracene compounds different from the organic compound, the one or more kinds of anthracene compounds each having a hydrogen atom at at least one of positions 9 and 10, the method comprising a step of:
reducing the content of the one or more kinds of anthracene compounds,
wherein the reducing is repeated until a total concentration of the one or more kinds of anthracene compounds is 100 ppm or less, and
wherein the organic compound is a polycyclic aromatic hydrocarbon.

* * * * *